(12) United States Patent
Milne et al.

(10) Patent No.: US 12,280,213 B2
(45) Date of Patent: *Apr. 22, 2025

(54) COMPONENTS FOR MEDICAL CIRCUITS

(71) Applicant: Fisher & Paykel Healthcare Limited, Auckland (NZ)

(72) Inventors: Robert Andrew David Milne, Auckland (NZ); Timothy Dee Gierke, Wilmington, DE (US)

(73) Assignee: Fisher & Paykel Healthcare Limited, Auckland (NZ)

( * ) Notice: Subject to any disclaimer, the term of this patent is extended or adjusted under 35 U.S.C. 154(b) by 0 days.

This patent is subject to a terminal disclaimer.

(21) Appl. No.: 18/333,343

(22) Filed: Jun. 12, 2023

(65) Prior Publication Data

US 2024/0017034 A1     Jan. 18, 2024

Related U.S. Application Data

(63) Continuation of application No. 16/867,832, filed on May 6, 2020, now Pat. No. 11,712,534, which is a
(Continued)

(51) Int. Cl.
*A61M 16/00* (2006.01)
*A61M 16/08* (2006.01)
(Continued)

(52) U.S. Cl.
CPC .... *A61M 16/0883* (2014.02); *A61M 16/0808* (2013.01); *A61M 16/0816* (2013.01);
(Continued)

(58) Field of Classification Search
CPC .......... A61M 16/0883; A61M 16/0833; A61M 16/1095; A61M 16/161; A61M 16/0808;
(Continued)

(56) References Cited

U.S. PATENT DOCUMENTS 3,670,726 A    6/1972   Mahon
4,051,847 A   10/1977   Henkin
(Continued)

FOREIGN PATENT DOCUMENTS

CN            1210020        3/1999
CN            1314192        9/2001
(Continued)

OTHER PUBLICATIONS

Claim Construction Order in the United States District Court of the Central District of California (Case No. 8:19-cv-00835-JVS-DFM) dated Mar. 27, 2020.
(Continued)

*Primary Examiner* — Steven O Douglas
(74) *Attorney, Agent, or Firm* — VIA LLP

(57) ABSTRACT

An expiratory limb is provided that is configured to remove humidified gases from a patient and configured to provide improved drying performance by providing a tailored temperature profile along the limb. Limbs for providing humidified gases to and/or removing humidified gases from a patient are also provided, the limbs having improved gas residence time at constant volumetric flow rate. The improved residence time can be achieved by providing a limb comprising multiple lumens.

19 Claims, 13 Drawing Sheets

Related U.S. Application Data continuation of application No. 14/777,438, filed as application No. PCT/NZ2014/000039 on Mar. 14, 2014, now Pat. No. 10,682,484.

(60) Provisional application No. 61/925,099, filed on Jan. 8, 2014, provisional application No. 61/790,424, filed on Mar. 15, 2013, provisional application No. 61/789,754, filed on Mar. 15, 2013.

(51) Int. Cl.
*A61M 16/10* (2006.01)
*A61M 16/16* (2006.01)

(52) U.S. Cl.
CPC .... *A61M 16/0833* (2014.02); *A61M 16/0875* (2013.01); *A61M 16/1045* (2013.01); *A61M 16/1095* (2014.02); *A61M 16/161* (2014.02); *A61M 16/16* (2013.01); *A61M 2205/3368* (2013.01); *A61M 2205/3633* (2013.01); *A61M 2205/3673* (2013.01); *A61M 2205/50* (2013.01)

(58) Field of Classification Search
CPC .......... A61M 16/0816; A61M 16/0875; A61M 16/1045; A61M 16/16; A61M 2205/3368; A61M 2205/3633; A61M 2205/3673; A61M 2205/50
See application file for complete search history.

(56) References Cited

U.S. PATENT DOCUMENTS

| | | |
|---|---|---|
| 4,265,235 A | 5/1981 | Fukunaga |
| 4,456,058 A | 6/1984 | Powell |
| 4,698,890 A | 10/1987 | Neaves |
| 4,727,871 A | 3/1988 | Smargiassi et al. |
| 5,015,013 A | 5/1991 | Nadin |
| 5,079,802 A | 1/1992 | Blasé et al. |
| 5,188,609 A | 2/1993 | Bayless et al. |
| 5,233,996 A | 8/1993 | Coleman et al. |
| 5,284,160 A | 2/1994 | Dryden |
| 5,454,061 A | 9/1995 | Carlson |
| 5,501,212 A | 3/1996 | Psaros |
| 5,614,588 A | 3/1997 | Steenblock |
| 5,918,640 A | 7/1999 | Orcutt |
| 5,924,456 A | 7/1999 | Simon |
| 5,983,896 A | 11/1999 | Fukunaga et al. |
| 5,988,164 A | 11/1999 | Paluch |
| 6,078,730 A | 6/2000 | Huddart et al. |
| 6,098,666 A | 8/2000 | Wells |
| 6,209,539 B1 | 4/2001 | Loescher |
| 6,513,767 B1 | 2/2003 | Rodgers |
| 6,568,716 B1 | 5/2003 | Fleber |
| 6,769,431 B2 | 8/2004 | Smith et al. |
| 6,854,694 B1 | 2/2005 | Van Etten |
| 6,874,500 B2 | 4/2005 | Fukunaga |
| 7,140,366 B2 | 11/2006 | Smith et al. |
| 7,146,979 B2 | 12/2006 | Seakins et al. |
| 7,382,531 B2 | 6/2008 | Tsuchiya et al. |
| 7,472,707 B2 | 1/2009 | Wood |
| 8,037,882 B2 | 10/2011 | Smith |
| 9,032,952 B2 | 5/2015 | Grilllot et al. |
| 9,602,020 B2 | 3/2017 | Kondo et al. |
| 10,500,364 B2 | 12/2019 | Milne et al. |
| 10,532,177 B2 | 1/2020 | Hermez et al. |
| 10,682,484 B2 | 6/2020 | Milne et al. |
| 10,688,268 B2 | 6/2020 | Gulliver et al. |
| 11,413,418 B2 | 8/2022 | Milne et al. |
| 11,712,534 B2 | 8/2023 | Milne |
| 2002/0179166 A1 | 12/2002 | Houston |
| 2003/0005554 A1 | 1/2003 | Nagayasu |
| 2003/0188746 A1 | 10/2003 | Daugherty |
| 2004/0099268 A1 | 5/2004 | Smith et al. |
| 2005/0061326 A1 | 3/2005 | Payne |
| 2005/0177056 A1 | 8/2005 | Giron |
| 2008/0105257 A1 | 5/2008 | Klasek |
| 2011/0253136 A1 | 10/2011 | Sweeney |
| 2012/0125333 A1 | 5/2012 | Bedford et al. |
| 2012/0125334 A1 | 5/2012 | Korneff |
| 2016/0022949 A1 | 1/2016 | Milne |
| 2016/0045702 A1 | 2/2016 | Milne |
| 2020/0121882 A1 | 4/2020 | Milne |
| 2020/0360642 A1 | 11/2020 | Milne |
| 2023/0052731 A1 | 2/2023 | Milne |

FOREIGN PATENT DOCUMENTS

| | | |
|---|---|---|
| CN | 1341463 | 3/2002 |
| CN | 101022881 | 8/2007 |
| CN | 101044795 | 9/2007 |
| CN | 101146517 | 3/2008 |
| CN | 101306216 | 11/2008 |
| CN | 101310789 | 11/2008 |
| CN | 101541367 A | 9/2009 |
| CN | 101641130 | 2/2010 |
| CN | 101808689 A | 8/2010 |
| CN | 101927050 | 12/2010 |
| CN | 102105189 | 6/2011 |
| CN | 202128784 | 2/2012 |
| CN | 102753229 A | 10/2012 |
| DE | 202006007397 U1 | 9/2007 |
| EP | 0535379 | 10/1996 |
| EP | 1514570 A2 | 3/2005 |
| GB | 2142376 | 7/1984 |
| GB | 2139110 | 11/1984 |
| GB | 2252515 | 8/1992 |
| GB | 2429653 A | 3/2007 |
| JP | H05237332 | 9/1993 |
| JP | 2000-024111 | 1/2000 |
| JP | 2000500359 | 1/2000 |
| JP | 2001314508 | 11/2001 |
| JP | 2002058741 A | 2/2002 |
| JP | 2007530157 | 11/2007 |
| JP | 2008006067 | 1/2008 |
| JP | 2010508875 | 3/2010 |
| JP | 2011512889 | 4/2011 |
| WO | WO 2004/105847 | 12/2004 |
| WO | WO 2010/131189 | 11/2010 |
| WO | WO 2011/077250 | 6/2011 |
| WO | WO 2011/149362 | 12/2011 |
| WO | WO 2011/162622 | 12/2011 |
| WO | 2012072997 | 6/2012 |
| WO | 2012154064 A2 | 11/2012 |
| WO | 2012164407 A1 | 12/2012 |
| WO | 2013002655 A2 | 1/2013 |

OTHER PUBLICATIONS

Quisona—A clip with opposing sprung jaws, the jaws are intended for clipping to a bed sheet, the inner of the clip collar is provided for locating of a tube.
U.S. Appl. No. 14/777,438, filed Sep. 15, 2015, Milne.
U.S. Appl. No. 14/777,440, filed Sep. 15, 2015, Milne.

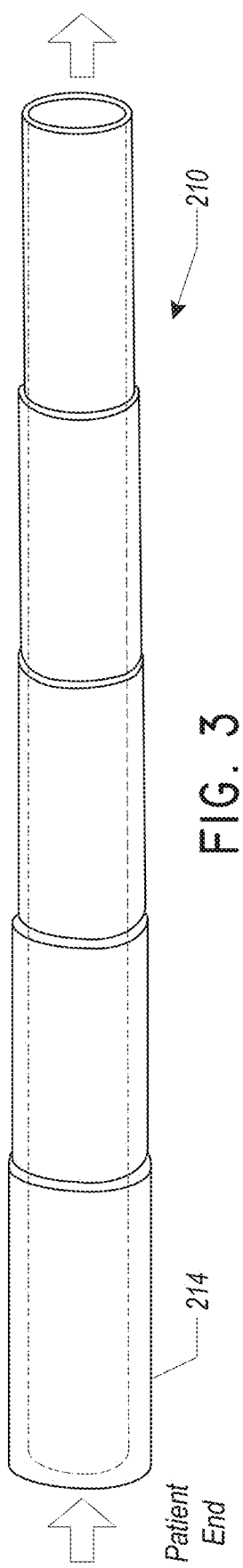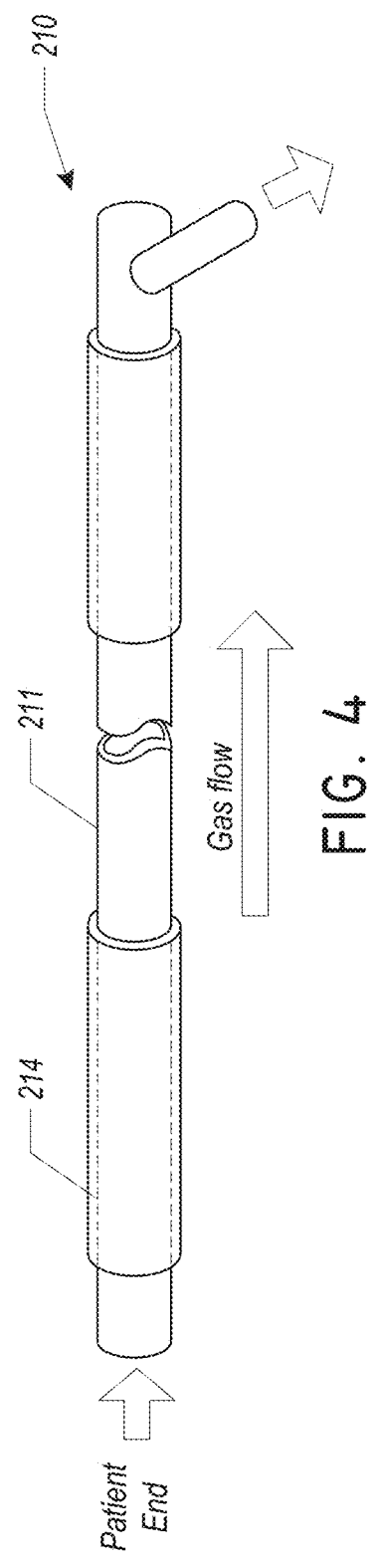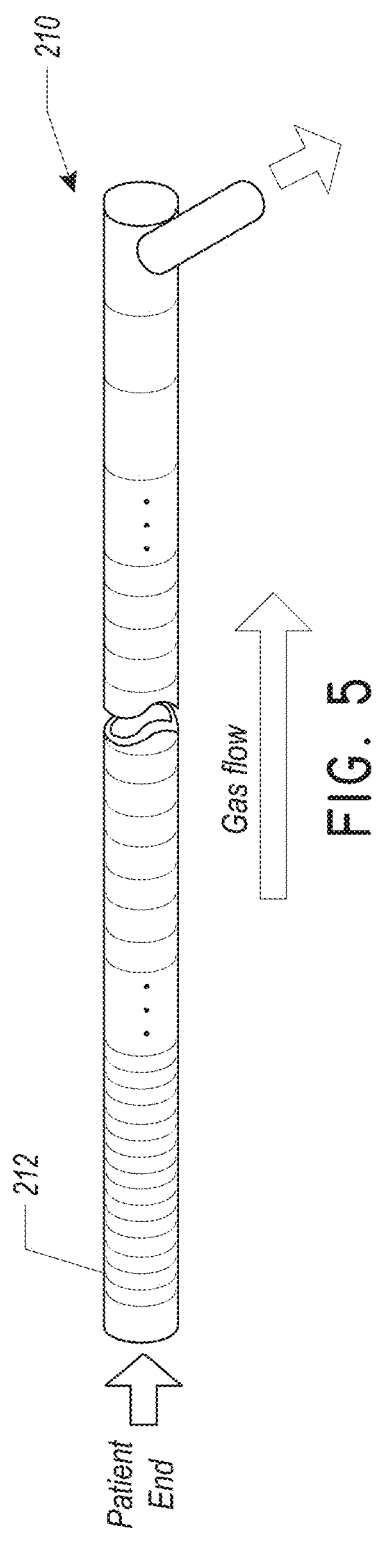

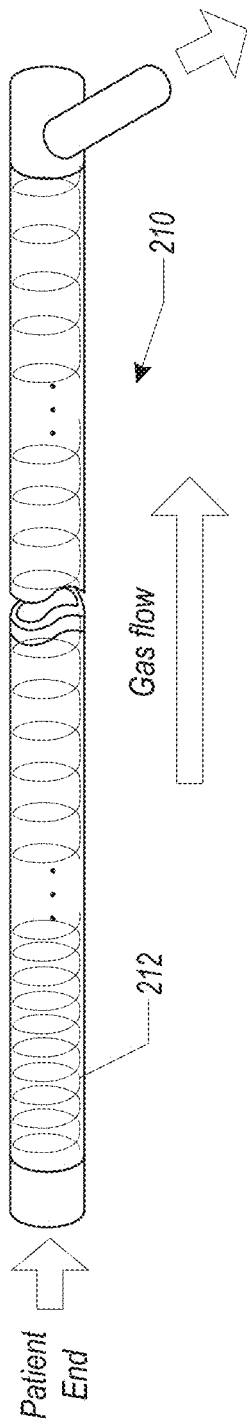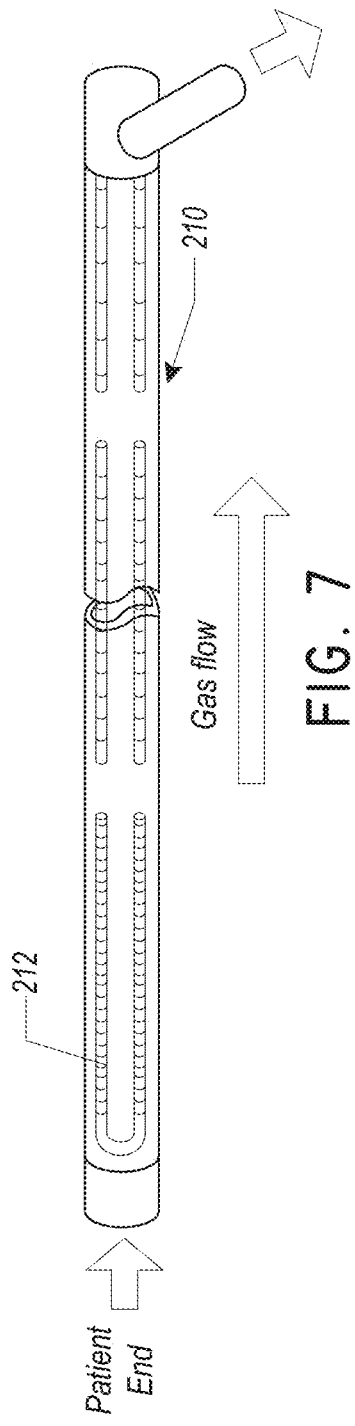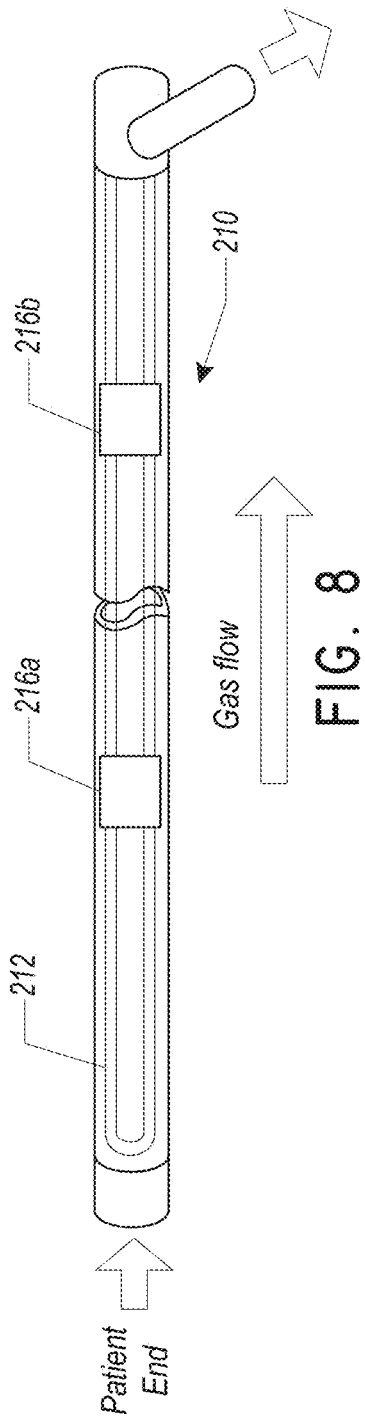

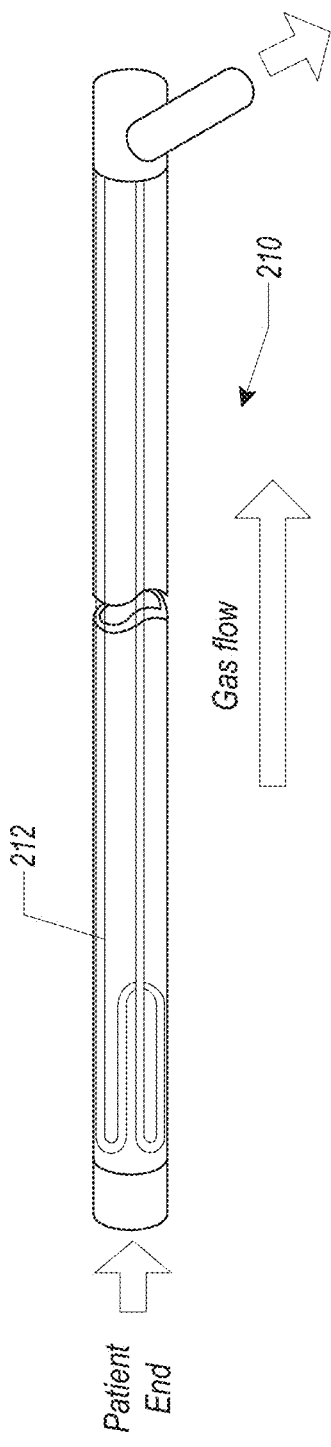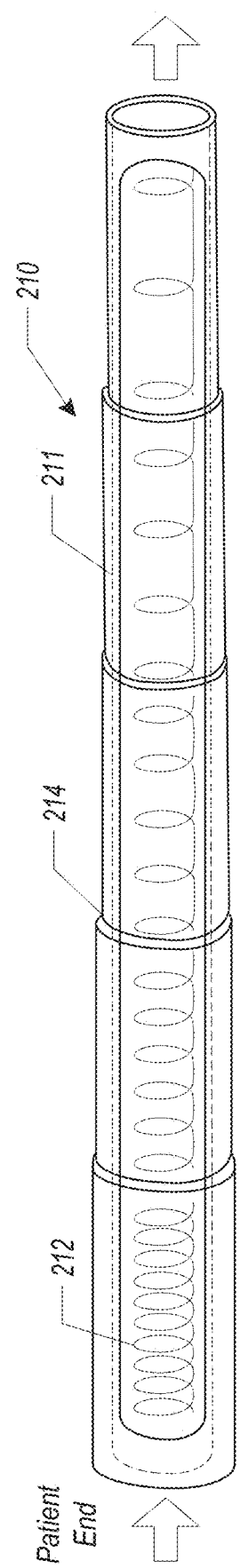
FIG. 9
FIG. 10

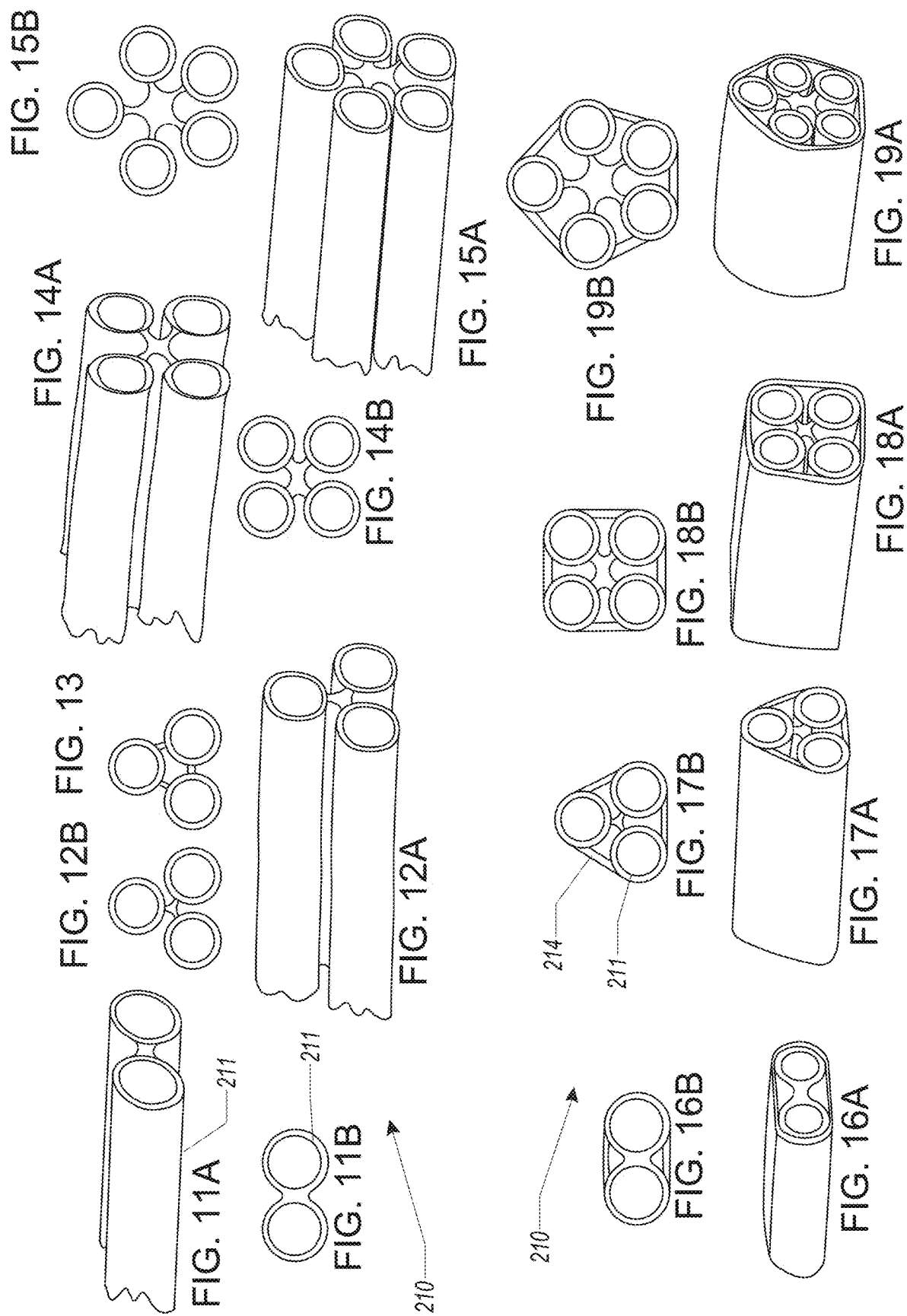

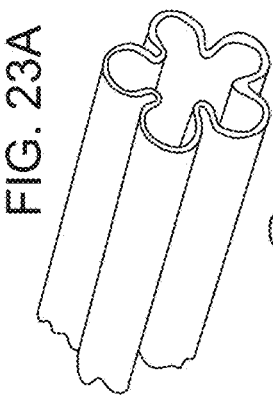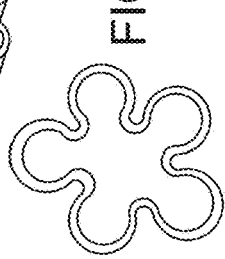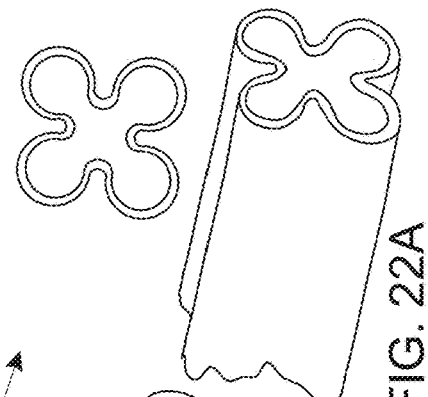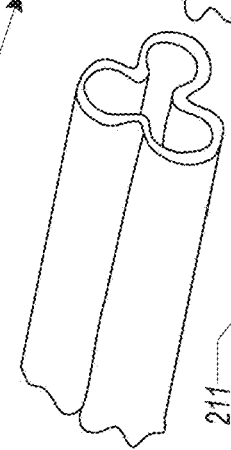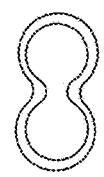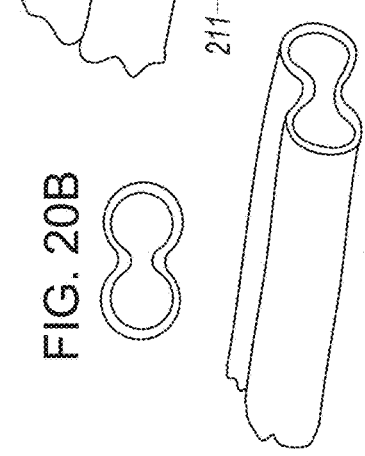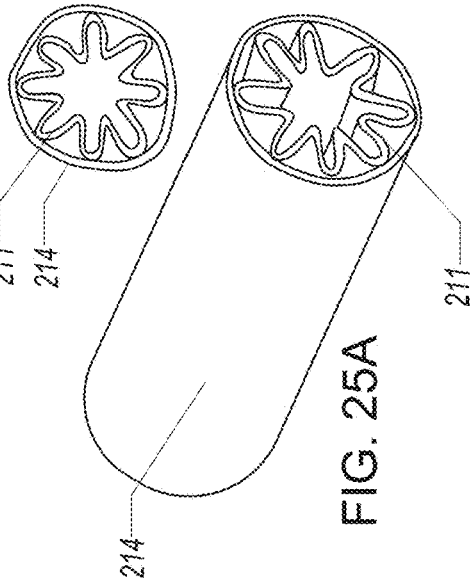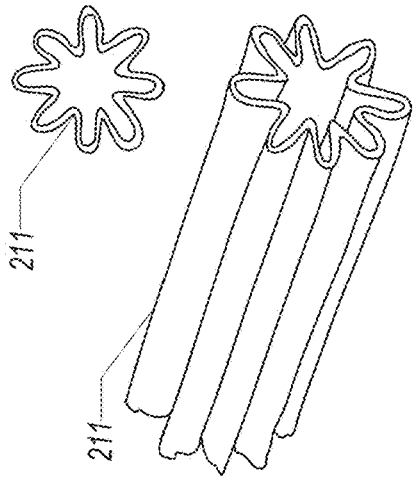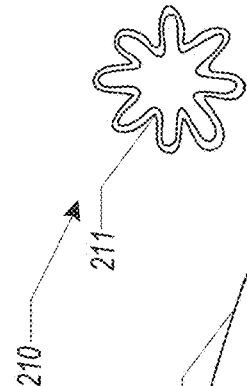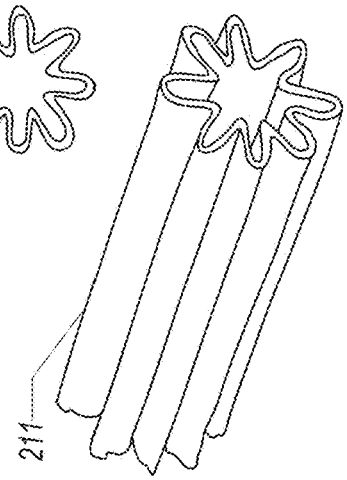

COMPONENTS FOR MEDICAL CIRCUITS

INCORPORATION BY REFERENCE

This application is a continuation of U.S. patent application Ser. No. 16/867,832, entitled COMPONENTS FOR MEDICAL CIRCUITS, filed May 6, 2020, which is a continuation of U.S. patent application Ser. No. 14/777,438, entitled "COMPONENTS FOR MEDICAL CIRCUITS," filed Sep. 15, 2015, now U.S. Pat. No. 10,682,484, which is a 371 national phase of PCT Application No. PCT/NZ2014/000039, entitled "COMPONENTS FOR MEDICAL CIRCUITS," filed Mar. 14, 2014, which claims the benefit of U.S. Provisional Application No. 61/790,424, entitled "DRYING EXPIRATORY LIMB WITH TAILORED TEMPERATURE PROFILE," filed Mar. 15, 2013, U.S. Provisional Application No. 61/789,754, entitled "DRYING EXPIRATORY LIMB WITH TAILORED TEMPERATURE PROFILE AND MULTI-LUMEN CONFIGURATION," filed Mar. 15, 2013, and U.S. Provisional Application No. 61/925,099, entitled "COMPONENTS FOR MEDICAL CIRCUITS," filed Jan. 8, 2014, each of which is incorporated by reference herein in its entirety.

BACKGROUND

Field

This disclosure relates generally to components for medical circuits, and in particular to components for medical circuits providing humidified gases to and/or removing humidified gases from a patient, such as in obstructive sleep apnea, neonatal, respiratory humidification, and surgical humidification systems including insufflation systems.

Description of Related Art

In medical circuits, various components transport naturally or artificially humidified gases to and from patients. For example, in some breathing circuits such as CPAP (continuous positive airway pressure) or assisted-breathing circuits, gases inhaled by a patient are delivered from a heater-humidification unit through an inspiratory limb to a patient interface, such as a mask. As another example, surgical humidification limbs can deliver humidified gas (commonly $CO_2$) into the abdominal cavity in insufflation circuits. This can help prevent "drying out" of the patient's internal organs, and can decrease the amount of time needed for recovery from surgery.

In these medical applications, the gases are preferably delivered in a condition having humidity near saturation level and at close to body temperature (usually at a temperature between 33° C. and 37° C.). Condensation or "rain-out" can form on the inside surfaces of components as high humidity gases cool. A need remains for components that allow for improved humidification and condensate management in medical circuits. Accordingly, an object of certain components and methods described herein is to ameliorate one or more of the problems of prior art systems, or at least to provide the public with a useful choice.

SUMMARY

Aspects of this disclosure relate to limbs for use in medical circuits. Limb is a broad term and is to be given its ordinary and customary meaning to a person of ordinary skill in the art (that is, it is not to be limited to a special or customized meaning) and includes, without limitation, tubes, conduits, and device components for transporting gases. The limbs disclosed herein can be applied in a variety of applications that would benefit from increasing the residence time of a gas flow (that is, the average length of time during which a volume of gas is in the limb).

Certain embodiments of this disclosure relate to an expiratory limb leading away from a patient where the absolute humidity and dew point of the gas stream flowing away from the patient interface is reduced in a tailored and controlled fashion to eliminate condensation. This application is suitable for several medical environments including, without limitation, respiratory humidification and neonatal applications. When used in applications that transfer humidified air away from a patient, certain limbs described herein are capable of realizing reduced dew points over commercial products, such as Evaqua 2™ conduits (Fisher & Paykel Healthcare Ltd., Auckland, New Zealand).

Additional embodiments of this disclosure relate to humidifying a gas stream flowing towards the patient. In particular, at least one embodiment relates to a limb suitable for use in a humidification unit. This application is suitable for several medical environments including, without limitation, obstructive sleep apnea (such as CPAP) and surgical humidification applications. When used in applications that transfer humidified air to a patient, certain limbs described herein are capable of realizing increased dew points over previous commercial products.

The systems, methods and devices described herein have innovative aspects, no single one of which is indispensable or solely responsible for their desirable attributes. Without limiting the scope of the claims, some of the advantageous features will now be summarized.

In general, an expiratory limb is configured to dry a gas as it passes through the expiratory limb prior to reaching a ventilator. The expiratory limb can be configured to dry the gas sufficiently to reduce or eliminate condensation in the ventilator. Drying can be limited at least in part by a surface area of the limb and/or a residence time of the gas in the expiratory limb at constant volumetric flow rate. Certain embodiments include the realization that it may be advantageous to provide a drying expiratory limb that provides a tailored temperature profile of the gas along the expiratory limb to increase drying, to reduce or prevent rain out along the limb, and/or to reduce or prevent condensation in the ventilator.

In some embodiments, an improved or optimized drying of the gas within a drying expiratory limb is accomplished by controlling the temperature of the gas as it passes along the drying expiratory limb to maintain a difference between the gas temperature and its dew point temperature approximately constant. In some embodiments, this temperature difference is less than about 2° C., less than about 1.5° C., or between about 0.9° C. and about 1° C. In some embodiments, an improved or optimized drying of the gas within the drying expiratory limb is accomplished by keeping the relative humidity of the gas between about 90% and about 99%, between about 95% and about 99%, or between about 95% and about 97%. In some embodiments, this may be accomplished by keeping the dew point temperature and absolute humidity approximately linear along the length of the expiratory limb. In some embodiments, the temperature drop of the gas from the beginning of the limb to about the first 300 mm or 400 mm of the drying expiratory limb is less than 0.01° C./mm or between 0° C./mm and about 0.009° C./mm and the total temperature drop across the expiratory limb length is less than about 10° C., or between about 3° C.

and about 10° C. Accordingly, the drying expiratory limbs and temperature control mechanisms disclosed herein can be configured to tailor a temperature profile of the gas to increase or optimize drying of the gas, to reduce or eliminate rain out in the limb, and/or to reduce or eliminate condensation in the ventilator. In some embodiments, a drying expiratory limb is disclosed that provides an optimal drying of a gas where the optimal drying is where no condensation occurs in the limb or in the ventilator through a tailored temperature control process.

Some embodiments provide for a drying expiratory limb for use in a respiratory circuit which can include a wall having a first end and a second end separated by an expiratory limb length. The wall defines a space within and at least a part of said wall comprises a breathable material configured to allow transmission of water vapor but substantially prevent transmission of liquid water. The drying expiratory limb includes a first opening in the first end of the wall, the first opening configured to receive a gas at a first temperature and a first relative humidity. The drying expiratory limb includes a second opening in the second end of the wall configured to allow the gas to exit the drying expiratory limb, the gas having a second temperature and a second relative humidity upon exiting the drying expiratory limb. The drying expiratory limb is configured such that a difference between a temperature of the gas and a dew point temperature of the gas along the drying expiratory limb length is approximately constant.

In some aspects of the embodiment, the drying expiratory limb further includes an insulating material attached to an outer surface of the wall. The insulating material can be configured to control the temperature drop of the gas to increase drying of the gas along the expiratory limb length. In some embodiments, an amount of the insulating material is substantially constant along the expiratory limb length. The amount of the insulating material can vary along the expiratory limb length.

In some aspects, the drying expiratory limb can include a heater wire configured to selectively receive electrical power to provide heat to the gas in the drying expiratory limb. In some aspects, the heater wire is configured to control the temperature drop of the gas to increase drying of the gas along the expiratory limb length. In a further aspect, the drying expiratory limb includes two or more heaters that are configured to control the temperature of the gas to be above the dew point temperature by a targeted amount. In another aspect, the heater wire has varying pitch spacing along the expiratory limb length, and, in some implementations, the pitch spacing increases with distance from the first end. In some implementations, the heater wire comprises at least two sections, the two sections being configured to be independently controlled using control circuitry.

In some aspects, a flow rate of the drying expiratory limb is configured to improve breathability. For example, a cross-section of the drying expiratory limb can be increased to improve breathability.

In some aspects, the residence time is increased to improve breathability. In some aspects, a profile of an absolute humidity of the gas is substantially parallel to a profile of a dew point temperature of the gas. In some aspects, the drying expiratory limb is configured to substantially eliminate rain out at the first end of the limb and at the second end of the limb. In some aspects, the drying expiratory limb is configured to substantially eliminate rain out at a ventilator positioned at the second end of the limb.

Some embodiments provide for a drying expiratory limb for use in a respiratory circuit. The drying expiratory limb includes a wall having a first end and a second end separated by an expiratory limb length, the wall defining a space within and wherein at least a part of said wall comprises a breathable material configured to allow transmission of water vapor but substantially prevent transmission of liquid water. The drying expiratory limb includes a first opening in the first end of the wall, the first opening configured to receive a gas at a first temperature and a first relative humidity. The drying expiratory limb includes a second opening in the second end of the wall configured to allow the gas to exit the drying expiratory limb, the gas having a second temperature and a second relative humidity upon exiting the drying expiratory limb. The drying expiratory limb is configured such that the first relative humidity and the second relative humidity are approximately equal and a relative humidity of the gas at any point along the drying expiratory limb is approximately equal to the first relative humidity.

In some aspects, the relative humidity of the gas is at least about 95%, or at least about 99%. In some aspects, a decrease in temperature along the expiratory limb length is controlled according to a drying rate to keep the relative humidity at a targeted humidity value, where the targeted humidity value is between about 90% and about 99%, between about 95% and about 99%, or between about 95% and about 97%.

Some embodiments provide for a drying expiratory limb of a breathing circuit, the drying expiratory limb including a wall having a first end and a second end separated by an expiratory limb length, the wall defining a space within and wherein at least a part of said wall comprises a breathable material configured to allow transmission of water vapor but substantially prevent transmission of liquid water. The drying expiratory limb can include a first opening in the first end of the wall, the first opening configured to receive a gas at a first temperature and a first relative humidity. The drying expiratory limb can include a second opening in the second end of the wall configured to allow the gas to exit the drying expiratory limb, the gas having a second temperature and a second relative humidity upon exiting the drying expiratory limb. The drying expiratory limb can be configured such that a temperature of the gas remains above a dew point temperature of the gas along the drying expiratory limb length. In some aspects, the drying expiratory limb is configured such that a difference in temperature of the gas and the dew point temperature of the gas along the drying expiratory limb length is approximately constant.

In some aspects, the drying expiratory limb also includes an insulating material on an outer surface of the wall. In a further aspect, the insulating material is configured to control the temperature of the gas to be between about 0.9° C. and 1° C. above the dew point temperature. In another aspect, an amount of the insulating material is substantially constant along the expiratory limb length. In another aspect, an amount of the insulating material varies along the expiratory limb length.

In some aspects, a rate of temperature decrease from the first end to a distance of about 300 mm from the first end is less than or equal to about 0.01° C./mm.

In some aspects, the drying expiratory limb further includes a heater wire configured to selectively receive electrical power to provide heat to the gas in the drying expiratory limb. In a further aspect, the heater wire is configured to control the temperature of the gas to be between about 0.9° C. and 1° C. above the dew point temperature. In another aspect, the drying expiratory limb further includes a second heater that is configured to control the rate of temperature decrease of the gas. In another aspect, the heater wire has varying pitch spacing along the expiratory limb length. In a further aspect, the pitch spacing increases with distance from the first end. In another aspect, the heater wire comprises at least two sections, the two sections being configured to be independently controlled using control circuitry.

In some aspects, a residence time of the drying expiratory limb is configured to improve breathability. In a further aspect, a residence time of the drying expiratory limb is decreased to improve breathability.

In some aspects, a profile of an absolute humidity of the gas is substantially parallel to a profile of the dew point temperature of the gas.

In some aspects, the drying expiratory limb is configured to substantially eliminate rain out at the first end of the wall and at the second end of the wall.

Some embodiments provide for a drying expiratory limb of a breathing circuit and the drying expiratory limb includes a wall having a first end and a second end separated by an expiratory limb length, the wall defining a space within and wherein at least a part of said wall comprises a breathable material configured to allow transmission of water vapor but substantially prevent transmission of liquid water. The drying expiratory limb includes a first opening in the first end of the wall, the first opening configured to receive a gas at a first temperature and a first relative humidity. The drying expiratory limb includes a second opening in the second end of the wall configured to allow the gas to exit the drying expiratory limb, the gas having a second temperature and a second relative humidity upon exiting the drying expiratory limb. The drying expiratory limb is configured such that the first relative humidity and the second relative humidity are approximately between about 90% and about 99%.

In some aspects, the first relative humidity of the gas or the second relative humidity of the gas or both are at least about 95%. In some aspects, the first relative humidity of the gas or the second relative humidity of the gas or both are at least about 99%. In some aspects, a decrease in temperature along the expiratory limb length is controlled according to a drying rate to keep a relative humidity of the gas along the expiratory limb length within a targeted relative humidity range. In a further aspect, the targeted relative humidity range is between about 90% and about 99%.

Some embodiments provide for a drying expiratory limb of a breathing circuit and the drying expiratory limb includes a wall having a first end and a second end separated by an expiratory limb length, the wall defining a space within and wherein at least a part of said wall comprises a breathable material configured to allow transmission of water vapor but substantially prevent transmission of liquid water. The drying expiratory limb includes a first opening in the first end of the wall, the first opening configured to receive a gas at a first temperature and a first relative humidity. The drying expiratory limb includes a second opening in the second end of the wall configured to allow the gas to exit the drying expiratory limb, the gas having a second temperature and a second relative humidity upon exiting the drying expiratory limb. The drying expiratory limb is configured such that a temperature of the gas remains approximately above a dew point temperature of the gas along the drying expiratory limb length, and a relative humidity of the gas remains approximately between about 90% and 99%.

In some aspects, the drying expiratory limb is configured such that the temperature of the gas remains approximately 1° C. above the dew point temperature of the gas along the drying expiratory limb length.

Some embodiments provide for a drying expiratory limb of a breathing circuit and the drying expiratory limb includes a wall having a first end and a second end separated by an expiratory limb length, the wall defining a space within and wherein at least a part of said wall comprises a breathable material configured to allow transmission of water vapor but substantially prevent transmission of liquid water. The drying expiratory limb includes a first opening in the first end of the wall, the first opening configured to receive a gas at a first temperature and a first relative humidity. The drying expiratory limb includes a second opening in the second end of the wall configured to allow the gas to exit the drying expiratory limb, the gas having a second temperature and a second relative humidity upon exiting the drying expiratory limb. The drying expiratory limb is configured such that a temperature of the gas remains approximately 1° C. above a dew point temperature of the gas along the drying expiratory limb length.

Some embodiments provide for a limb having a multi-lumen design for delivering humidified gas to or from a patient. Such a limb is particularly useful for delivering and drying humidified gas from a patient. The limb includes a multi-lumen configuration, each lumen having a first end and a second end and a space within the lumen defined by a wall, and at least a part of said wall comprises a breathable material configured to allow transmission of water vapor but substantially prevent transmission of liquid water. The limb includes a gas entry port configured to receive a gas at an entry temperature and an entry relative humidity for transmission along the limb. The limb includes a gas exit port configured to allow the gas to exit the limb, the gas having an exit temperature and an exit relative humidity upon exiting the limb. The limb can be configured to increase a drying of the gas as it passes through the limb as compared to an expiratory limb comprising a single lumen of a similar size and a similar material. The limb can be configured such that a difference between a temperature of the gas and a dew point temperature of the gas along the limb length is approximately constant.

In some aspects, the multi-lumen configuration comprises a plurality of conduits. In a further aspect, the plurality of conduits is configured to increase residence time of gas in the limb at constant volumetric flow rate.

In some aspects, the limb further includes a heater wire configured to provide heat to the gas passing through the expiratory limb. In some aspects, the heater wire is configured to deliver a greater amount of heat to the gas near the entry port of the limb than to the gas near the exit port.

Some embodiments provide for a limb having a multi-lumen design for delivering humidified gas to or from a patient in a medical circuit. As discussed above, such a limb is particularly useful for delivering and drying humidified gas from a patient. The limb includes a multi-lumen configuration, each lumen having a first end and a second end and a space within the lumen defined by a wall, and at least a part of said wall comprises a breathable material configured to allow transmission of water vapor but substantially prevent transmission of liquid water. The limb includes a gas entry port configured to receive a gas at an entry temperature and an entry relative humidity for transmission along the limb. The limb includes a gas exit port configured to allow the gas to exit the limb, the gas having an exit temperature and an exit relative humidity upon exiting the limb.

In some embodiments, the limb is configured to increase a drying of the gas as it passes through the limb as compared to an expiratory limb comprising a single lumen of a similar size and a similar material. The limb can be configured such that the first relative humidity and the second relative humidity are approximately equal and a relative humidity of the gas at any point along the limb is approximately equal to the first relative humidity.

Some embodiments provide for a limb of a medical circuit and the limb includes a multi-lumen configuration, wherein each lumen has a first end and a second end and a space within the lumen defined by a wall, at least a part of said wall comprises a breathable material configured to allow transmission of water vapor but substantially prevent transmission of liquid water. The limb includes a gas entry port configured to receive a gas at an entry temperature and an entry relative humidity for transmission along the expiratory limb. The limb includes a gas exit port configured to allow the gas to exit the expiratory limb, the gas having an exit temperature and an exit relative humidity upon exiting the expiratory limb. The multi-lumen design can be configured to increase a drying of the gas as it passes through the expiratory limb as compared to an expiratory limb comprising a single lumen of a similar size and a similar material. The limb can be configured such that a temperature of the gas remains above a dew point temperature of the gas along the limb length.

In some aspects, the multi-lumen configuration comprises a plurality of conduits. In a further aspect, the plurality of conduits is configured to decrease a flow rate in each lumen.

In some aspects, the limb further includes a heater wire configured to provide heat to the gas passing through the expiratory limb. In a further aspect, the heater wire is configured to deliver a greater amount of heat to the gas near the entry port of the expiratory limb than to the gas near the exit port.

In some aspects, the number of lumens is less than or equal to 5. In a further aspect, the number of lumens is equal to 3.

Some embodiments provide for a limb of a medical circuit and the limb includes a multi-lumen configuration, wherein each lumen has a first end and a second end and a space within the lumen defined by a wall, at least a part of said wall comprises a breathable material configured to allow transmission of water vapor but substantially prevent transmission of liquid water. The limb includes a gas entry port configured to receive a gas at an entry temperature and an entry relative humidity for transmission along the expiratory limb. The limb includes a gas exit port configured to allow the gas to exit the expiratory limb, the gas having an exit temperature and an exit relative humidity upon exiting the expiratory limb. The multi-lumen design is configured to increase a drying of the gas as it passes through the expiratory limb as compared to an expiratory limb comprising a single lumen of a similar size and a similar material. The limb is configured such that the first relative humidity and the second relative humidity are approximately between about 90% and about 99%. In some aspects, the number of lumens is less than or equal to 5.

Some embodiments provide for a limb for use in a respiratory circuit and the limb includes a multi-lumen configuration comprising less than six lumens, wherein each lumen has a first end and a second end and a space within the lumen defined by a wall, at least a part of said wall comprises a breathable material configured to allow transmission of water vapor but substantially prevent transmission of liquid water. The limb includes a gas entry port configured to receive a gas at an entry temperature and an entry relative humidity for transmission along the expiratory limb. The limb includes a gas exit port configured to allow the gas to exit the expiratory limb, the gas having an exit temperature and an exit relative humidity upon exiting the expiratory limb. The multi-lumen design is configured to increase a drying of the gas as it passes through the expiratory limb as compared to an expiratory limb comprising a single lumen of a similar size and a similar material.

In at least one embodiment, a limb is provided that is suitable for use in a medical circuit, the limb comprising a first opening configured to receive a gas at a first temperature and a first relative humidity; a second opening configured to allow the gas to exit the limb, the gas having a second temperature and a second relative humidity; and a plurality of conduits each comprising a first end proximal the first opening, a second end proximal the second opening, and a wall extending between the end and the second end and defining a lumen within through which, when in use, gas flows in the direction of the first end toward the second end, and wherein at least a part of said wall comprises a breathable material configured to allow transmission of water vapor but substantially prevent transmission of liquid water.

In various embodiments, the foregoing limb has one, some, or all of the following properties, as well as properties described elsewhere in this disclosure. The breathable material can be foam. The material can have a substantially uniform thickness. The limb can comprise three conduits. The plurality of conduits can be corrugated. The void fraction of the foam material can be greater than 40%. The pneumatic compliance of the limb can be less than 10 mL/kPa/m. The void fraction of the foam material can be about 45%. The pneumatic compliance of the limb can be less than 3 mL/kPa/m. The plurality of conduits can be twisted or braided between the first opening and the second opening. The limb can further comprise one or more securing mechanisms configured to hold the plurality of conduits together. Each securing mechanism can comprise a plurality of lobes, and each of the conduits can pass through one of the lobes. Each securing mechanism can be a trefoil comprising a plurality of rings, and each of the conduits can pass through one of the rings. The limb can further comprise a connector comprising a unitary portion comprising an aperture defining the first opening or the second opening, a multipartite portion comprising a plurality of passages, each configured to connect to one of the plurality of conduits, and an internal ogive comprising a base attached to or formed on the multipartite portion between the plurality of passages, the ogive extending in the direction of the unitary portion and configured to direct the flow of gas from the multipartite portion to the unitary portion or from the unitary portion to the multipartite portion. The limb can further comprise at least one heater wire configured to provide heat to the gas passing through the limb. The wall of at least one of the conduits can encompass or have embedded thereon a heater wire configured to provide heat to the gas passing through the lumen. The lumen of at least one of the conduits can encompass a heater wire configured to provide heat to the gas passing through the lumen. The limb can be an expiratory limb and the first opening can be configured to receive gas from a patient interface.

In at least one embodiment, a device suitable for use with a limb of a medical circuit, comprises a unitary portion comprising an aperture configured to connect to a patient interface or a humidification device, a multipartite portion comprising a plurality of passages, each configured to connect to one of the plurality of conduits, and an internal ogive comprising a base attached to or formed on the multipartite portion between the plurality of passages, the ogive extending in the direction of the unitary portion and configured to direct the flow of gas from the multipartite portion to the unitary portion or from the unitary portion to the multipartite portion.

In various embodiments, the foregoing device has one, some, or all of the following properties, as well as properties described elsewhere in this disclosure. The multipartite portion can comprise three passages.

In at least one embodiment, a limb suitable for use in a medical circuit comprises a first opening configured to receive a gas at a first temperature and a first relative humidity; a second opening configured to allow the gas to exit the limb, the gas having a second temperature and a second relative humidity; and means for increasing the residence time of gas flow within the limb between the first opening and the second opening.

In various embodiments, the foregoing limb has one, some, or all of the following properties, as well as properties described elsewhere in this disclosure. The residence-time-increasing means can comprise a plurality of conduits between the first opening and the second opening, each of the conduits comprising a wall extending between the first opening and the second opening and defining a lumen within through which, when in use, gas flows in the direction of the first opening toward the second opening. At least a part of the wall can comprise a breathable foam material configured to allow transmission of water vapor but substantially prevent transmission of liquid water.

These and other embodiments are described in greater detail below.

BRIEF DESCRIPTION OF THE DRAWINGS

Throughout the drawings, reference numbers may be reused to indicate general correspondence between reference elements. The drawings are provided to illustrate example embodiments described herein and are not intended to limit the scope of the disclosure.

FIG. 3 illustrates a drying expiratory limb with varying insulation to control the temperature of the gas along the limb.

FIG. 4 illustrates a drying expiratory limb with two sections that include breathable insulation to control a temperature drop at a beginning of the limb and at an end of the limb.

FIG. 5 illustrates a drying expiratory limb having multiple heater wires that have a pitch spacing that is different in different sections.

FIG. 6 illustrates a drying expiratory limb having a coiled heater wire that has a pitch spacing that is different in different sections.

FIG. 7 illustrates a drying expiratory limb having a straight heater wire with zones of varying pitch spacing within the wire.

FIG. 8 illustrates a drying expiratory limb having multiple sections wherein a system is configured to independently control the different sections of heater wire.

FIG. 9 illustrates a drying expiratory limb having a heater wire that is folded back upon itself at a patient end to control a temperature drop at a front end of the drying expiratory limb.

FIG. 10 illustrates a drying expiratory limb combining a varying insulation layer with a heater wire with a varying pitch.

FIGS. 11A-19B illustrate various multi-lumen configurations for a drying expiratory limb.

FIGS. 20A-25B illustrate drying expiratory limbs configured to increase a surface area using different cross-section shapes.

DETAILED DESCRIPTION

Figure 1:
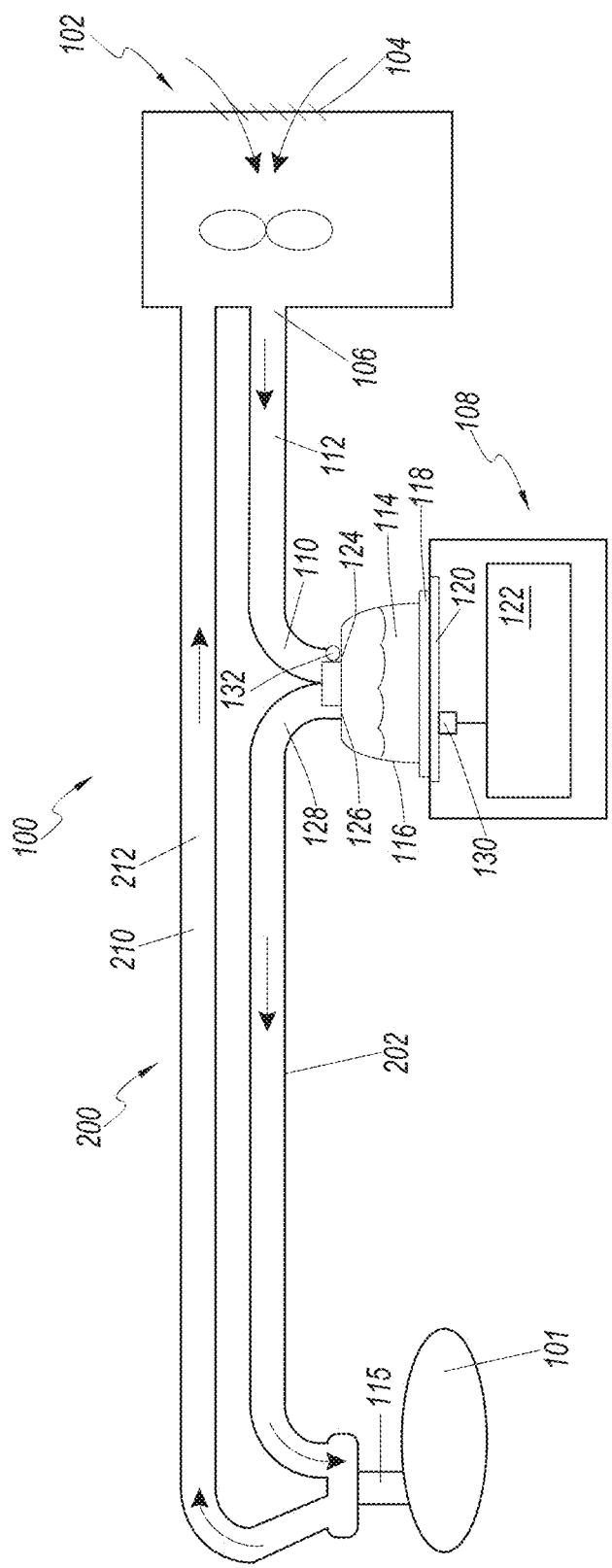
FIG. 1 illustrates an example respiratory system for delivering humidified gas to a user, the respiratory humidification system having a breathing circuit that includes a drying expiratory limb configured to have a linear temperature profile as a function of distance along the drying expiratory limb.

Certain embodiments and examples of limbs for conveying humidified gas in medical circuits are described herein. Those of skill in the art will appreciate that the disclosure extends beyond the specifically disclosed embodiments and/or uses and obvious modifications and equivalents thereof. Thus, it is intended that the scope of the disclosure not be limited by any particular embodiments described herein.

It is desirable to provide a breathable limb for use in a medical circuit. Breathable is used herein to mean appreciably permeable to water vapor and substantially impermeable to liquid water and the bulk flow of gases. Breathability can be desirable to reduce or prevent rain out. "Rain out," or condensation, can be a problem when high humidity gases within a limb come into contact with the walls of a limb at a lower temperature. However, rain out depends on many factors, including not only the temperature profile in the limb, but also the gas flow rate, component geometry, and the intrinsic breathability of the material used to form the component. In general, a breathable limb can be desirable because it allows water from a high-humidity gas flow within a limb to pass into a low-humidity environment, ameliorating the potential for rain out within the limb. Conversely, and depending upon the application, breathability can also be desirable to allow water from a high-humidity environment to pass into and thereby humidify a gas flow within a limb.

Furthermore, it can also be advantageous to control the temperature and/or relative humidity of the gas passing through the limb. Temperature and/or relative humidity control can limit or prevent condensation in a downsteam/upstream device or interface, rain out in the limb, to increase drying of the gas, or any combination of these.

Descriptions of limbs for conveying humidified gas in a medical circuit are presented herein that include breathable material configured to pass water vapor and to substantially prevent liquid water from passing through. Any suitable breathable material can be used. Nevertheless, particularly suitable breathable materials are described in PCT Publication WO 2011/077250, entitled "Components for Medical Circuits," filed Dec. 22, 2010, which is hereby incorporated by reference in its entirety and made a part of this specification. As described in that publication, the breathable material can be a breathable foamed material configured to allow the transmission of water vapor but substantially prevent the transmission of liquid water. The breathable foamed material can comprise a blend of polymers. The breathable foamed material can comprise a thermoplastic elastomer with a polyether soft segment. The breathable foamed material can comprise a copolyester thermoplastic elastomer with a polyether soft segment. The breathable foamed material can comprise a thermoplastic elastomer with a polyether soft segment.

As discussed in more detail below with reference at least to FIG. 1, expiratory limbs can be included in medical circuits. As used herein, an expiratory limb is broadly defined to mean a limb that transmits humidified gases from a patient in a medical circuit. Expiratory limbs are suitable for breathing circuits for use in respiratory applications. For an unheated expiratory limb, as the gas travels along the limb towards a ventilator, ambient, or gas source, the gas will cool at a rate that is higher than its drying rate. As a result, the temperature of the gas can drop below the dew point temperature, causing condensation to form inside the expiratory limb. For a heated expiratory limb, the gas may be kept at a high temperature for too long. As the gas dries, the relative humidity of the gas can drop (as the temperature of the gas is relatively constant over a portion of the limb), which impairs further drying, as drying is more efficient when the relative humidity is at or near about 100%. If the gas has not been dried enough, when the temperature drops in the ventilator then condensation can form in the ventilator.

Accordingly, it may be advantageous to improve or optimize drying along the length of the expiratory limb, which can be accomplished, in some embodiments, by maintaining the relative humidity at a substantially constant value. In some embodiments, improved or optimized drying may occur where the relative humidity remains between about 90% and about 99%, between about 95% and about 99%, or between about 95% and about 97%. It may also be advantageous to reduce the temperature of the gas along the length of the limb so that the temperature of the gas exiting the expiratory limb is at or near the temperature of the ventilator, gas source, or ambient.

An effective method of doing this is to have the humidity and/or temperature decrease in a tailored manner along the length of the limb. For example, it may be advantageous to tailor the rate of temperature decrease across the first portion of the expiratory limb so that it does not exceed about 0.01° C./mm, or so that the temperature drop is between about 0° C./mm and about 0.009° C./mm. In some embodiments, it may be advantageous to limit the rate of temperature decrease to the stated ranges from the beginning of the limb to about the first 300 mm or 400 mm of the expiratory limb. It may be advantageous to also limit the total temperature drop across the limb to be less than or equal to about 10° C. and/or between about 3° C. and 10° C. In some embodiments, drying within a limb is limited by the relative humidity. In some embodiments, it may be desirable to have the temperature drop in a linear or a nearly linear fashion along the limb.

Therefore, the expiratory limbs described herein have been configured to achieve the goals of reducing or eliminating rain out or condensation in the ventilator through controlling the environment within the limb. For example, for a gas with a relative humidity of about 95%, the expiratory limb can be configured to tailor the temperature profile such that the difference between the temperature of the gas and the dew point temperature is less than about 1.5° C., less than about 1° C., or between about 0.9° C. and about 1° C. The heating or insulation of the limb can be configured to keep the temperature within a "non-condensation window" which can be a temperature range that lies between the dew point temperature line and the absolute humidity line so that little or no condensation occurs within the expiratory limb or at the ventilator.

In some embodiments, an example temperature profile that reduces condensation, reduces rain out, and that provides the advantageous properties described herein can be where an initial temperature drop (e.g., from the patient interface) from the beginning of the limb to about the first 300 or 400 mm can have a slope that is between about 0° C./mm and about 0.01° C./mm. In some embodiments, a temperature profile that has a total drop in temperature between about 3° C. and about 10° C. may provide at least some of the advantages set forth herein.

Embodiments of expiratory limbs will be now described herein with reference to their use in a respiratory system. It is to be understood, however, that the limbs described herein can be used with a variety of applications where it is desirable to increase the residence time of a gas flow from a first environment to a second environment having different temperatures and/or humidity, such as incubation systems, surgical humidification systems, and the like.

FIG. 1 illustrates an example respiratory system 100 for delivering humidified gas to a user, the humidification system 100 having a breathing circuit 200 that includes an inspiratory limb 202 and an expiratory limb 210. The illustrated respiratory humidification system 100 comprises a pressurized gas source 102. In some implementations, the pressurized gas source 102 comprises a fan, blower, or the like. In some implementations, the pressurized gas source 102 comprises a ventilator or other positive pressure generating device. The pressurized gas source 102 comprises an inlet 104 and an outlet 106.

The pressurized gas source 102 provides a flow of fluid (e.g., oxygen, anesthetic gases, air or the like) to a humidification unit 108. The fluid flow passes from the outlet 106 of the pressurized gas source 102 to an inlet 110 of the humidification unit 108. In the illustrated configuration, the humidification unit 108 is shown separate of the pressurized gas source 102 with the inlet 110 of the humidification unit 108 connected to the outlet 106 of the pressurized gas source 102 with a conduit 112. In some implementations, the pressurized gas source 102 and the humidification unit 108 can be integrated into a single housing.

The gases flow through the inspiratory limb 202 to the patient 101 through a patient interface 115. The expiratory limb 210 also connects to the patient interface 115. The expiratory limb 210 is configured to move exhaled humidified gases away from the patient 101. Here, the expiratory limb 210 returns exhaled humidified gases from the patient interface 115 to the gases source 102. Alternatively, exhaled humidified gases can be passed directly to ambient surroundings or to other ancillary equipment, such as an air scrubber/filter (not shown). Any suitable patient interface 115 can be incorporated. Patient interface is a broad term and is to be given its ordinary and customary meaning to a person of ordinary skill in the art (that is, it is not to be limited to a special or customized meaning) and includes, without limitation, masks (such as face masks and nasal masks), cannulas, and nasal pillows. A patient interface usually defines a gases space which, when in use, receives warm humid breathing gases.

While other types of humidification units can be used with certain features, aspects, and advantages described in the present disclosure, the illustrated humidification unit 108 is a pass-over humidifier that comprises a humidification chamber 114 and an inlet 110 to the humidification chamber 114. In some implementations, the humidification chamber 114 comprises a body 116 having a base 118 attached thereto. A compartment can be defined within the humidification chamber 116 that is adapted to hold a volume of liquid that can be heated by heat conducted or provided through the base 118. In some implementations, the base 118 is adapted to contact a heater plate 120. The heater plate 120 can be controlled through a controller 122 or other suitable component such that the heat transferred into the liquid can be varied.

The controller 122 of the humidification unit 108 can control operation of various components of the respiratory humidification system 100. While the system as illustrated uses a single controller 122, multiple controllers can be used in other configurations. The multiple controllers can communicate or can provide separate functions and, therefore, the controllers need not communicate. In some implementations, the controller 122 may comprise a microprocessor, a processor, or logic circuitry with associated memory or storage that contains software code for a computer program. In such implementations, the controller 122 can control operation of the respiratory humidification system 100 in accordance with instructions, such as contained within the computer program, and also in response to internal or external inputs.

The body 116 of the humidification chamber 114 comprises a port 124 that defines the inlet 110, and a port 126 that defines an outlet 128 of the humidification chamber 114. As liquid contained within the humidification chamber 114 is heated, liquid vapor is mixed with gases introduced into the humidification chamber 114 through the inlet port 124. The mixture of gases and vapor exits the humidification chamber 114 through the outlet port 126.

The humidification system 100 includes a breathing circuit 200 comprising the inspiratory limb 202 connected to the outlet 128 that defines the outlet port 126 of the humidification unit 108. The inspiratory limb 202 conveys toward a user the mixture of gases and water vapor that exits the humidification chamber 114. The inspiratory limb 202 can include a heating element 206 positioned along the inspiratory limb 202, wherein the heating element 206 is configured to reduce condensation along the inspiratory limb 202, to control a temperature of gas arriving at the user, or both. The heating element 206 can raise or maintain the temperature of the gases and water vapor mixture being conveyed by the inspiratory limb 202. In some implementations, the heating element 206 can be a wire that defines a resistance heater. By increasing or maintaining the temperature of the gases and water vapor mixture leaving the humidification chamber 114, the water vapor is less likely to condense out of the mixture.

Expiratory Limb

The humidification system 100 includes an expiratory limb 210 configured to carry away expired gas from the user and deliver it to the gas source 102. The expiratory limb 210 can include a wall having a first end at the patient end to receive the expired or exhaled gas and a second end at the gas source 102, the two ends being separated by an expiratory limb length. The wall can define a space for the gas to travel (e.g., one or more lumens) and at least a portion of the wall can include a breathable material.

If the gas cools too quickly along the expiratory limb 210, the gas can become supersaturated as the water vapor cannot pass through the breathable layer quickly enough. This can cause, at least in part, rain out near the patient end of the expiratory limb 210. If the gas cools too slowly, rain out can form near the second end of the expiratory limb 210, where the relatively hot gas comes into contact with cooler air at the gas source 102 or ambient. To reduce or prevent rain out in the expiratory limb, characteristics of the gas or the expiratory limb 210 can be controlled. For example, by controlling the temperature profile of the gas and other variables in the expiratory limb 210, the breathability of the expiratory limb 210 can be improved. In some embodiments, the breathability of the expiratory limb 210 can increase by increasing transit time through the expiratory limb 210, which can be accomplished, in some embodiments, by decreasing a flow rate or by increasing a length of the passage through expiratory limb 210. Increasing the transit time through the expiratory limb may, in some implementations, increase heat loss of the gas through the expiratory wall. If this occurs too quickly, as stated above, rain out can occur. In some embodiments, providing a substantially linear temperature profile along the expiratory limb 210 and/or increasing a transit time through the expiratory limb 210 can increase the breathability of the expiratory wall by about 40% to about 70% or more. Accordingly, in some embodiments, the expiratory limb 210 can be configured to have a substantially linear temperature profile such that the temperature of the gas drops in a linear fashion across the length of the expiratory limb 210. Relatedly, in some embodiments, the expiratory limb 210 can be configured to keep a difference between the gas temperature and its dew point temperature substantially constant across the length of the expiratory limb 210. Similarly, in some embodiments, the expiratory limb 210 can be configured to keep a relative humidity of the gas at between about 95% to about 99% across the length of the expiratory limb 210.

In some embodiments, the expiratory limb 210 includes insulation configured to control a temperature profile in the expiratory limb. In some embodiments, the expiratory limb 210 includes an associated heating element 212 that is arranged along the expiratory limb 210, wherein the heating element 212 is configured to maintain a substantially linear temperature drop along the expiratory limb 202, to control a relative humidity of the gas, to control a temperature of the gas relative to its dew point temperature, or any combination of these.

The heating element 212 can be selectively controlled by the controller 122 in the humidification system 100 or through other means. The controller 122 can be configured to control the heating element 210, to receive feedback from sensors in the system, to provide logic to control power to the heating element 212, to adjust control of the heating element 212 in response to temperature readings from sensors, and the like. In some embodiments, the controller 122 includes a power source configured to deliver electrical power to the heating element 212. The controller 122, for example, can control an amount of heat delivered by the heating element 212 by delivering a variable power, a variable current, a variable voltage, or any combination of these to the heating element 212. The controller 122 can implement pulse-width-modulation to control the heating element 212. The controller 122 can apply a substantially constant electrical power until a desired temperature is reached within the expiratory limb 210. In some embodiments, the expiratory limb 210 includes one or more sensors configured to provide the controller or a user with information regarding the characteristics of the gas in the expiratory limb 210 which can include, for example, temperature, relative humidity, absolute humidity, or any combination of these and this information can be provided at one or more points along the expiratory limb 210. In some implementations, the heating element 206 can be a wire that defines a resistance heater.

In some embodiments, the expiratory limb 210 can include insulation in combination with the heating element 212. In some embodiments, the heating element 210 can be configured to provide zone heating capabilities such that different portions of the expiratory limb 210 receive different amounts of heat. This can be accomplished, for example, by using multiple heating wires or a single wire with different winding densities or pitch spacing at different points.

Example Expiratory Limbs with Tailored Temperature Profiles

Figure 2:
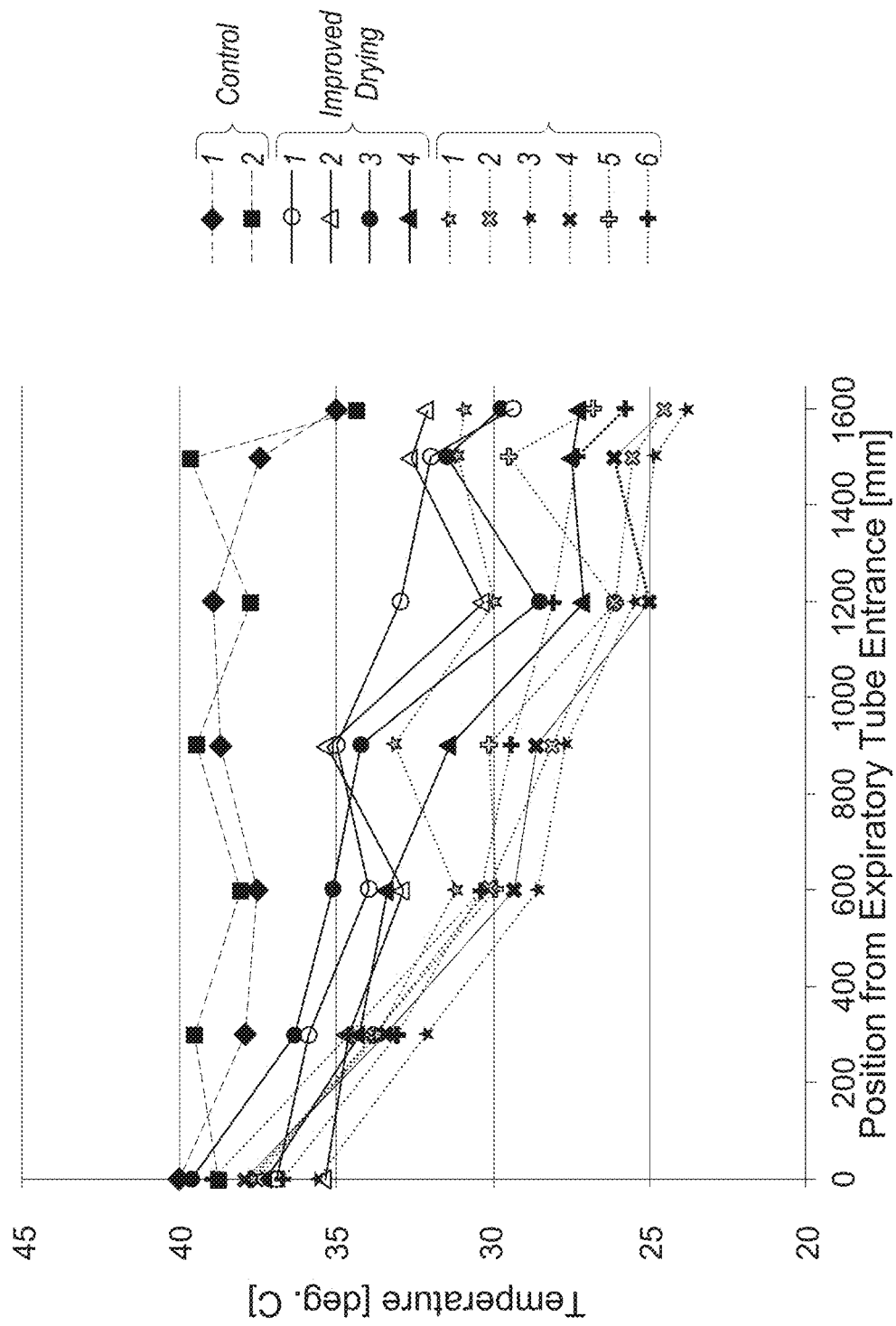
FIG. 2 illustrates a plot of a temperature of a gas as a function of position along an expiratory limb.

FIG. 2 illustrates a plot of a temperature of a gas as a function of position along an expiratory limb. The two plots listed as "Control" and shown with dashed lines illustrate some expiratory limbs that have been configured to dry gases using breathable materials. The four plots listed as "Improved Drying" and shown with solid lines illustrate results when using some embodiments described herein. They represent an improved or optimized drying of the gases through the expiratory limbs. The six plots listed as "Condensation" and shown with dotted lines represent expiratory limbs with temperature profiles that experience rain out or condensation within the limb or at the ventilator. These expiratory limbs experience a rate of temperature decrease from the beginning of the expiratory limb to about 300 mm or 400 mm that exceeds about 0.009° C./mm or about 0.01° C./mm and/or where the total temperature drop exceeds about 10° C. or is between about 3° C. and about 10° C.

Table 1 lists information related to the absolute humidity and dew point temperature for the temperature profiles of the two "Control" plots and the 4 "Improved Drying" plots in FIG. 2. The table lists the input absolute humidity ("AH In") and the output absolute humidity ("AH Out") and the dew point temperature ("DPT") of the exit gas.

TABLE 1

Absolute humidity and dew point temperature of example expiratory limbs

| Sample | AH In [mg/L] | AH Out [mg/L] | DPT [° C.] |
| --- | --- | --- | --- |
| Control 1 | 44.1 | 35.0 | 32.7 |
| Control 2 | 43.4 | 28.3 | 28.7 |
| Improved 1 | 43.4 | 25.1 | 26.5 |
| Improved 2 | 45.3 | 26.5 | 27.5 |
| Improved 3 | 42.3 | 26.3 | 27.4 |
| Improved 4 | 43.2 | 24.9 | 26.4 |

Example Expiratory Limbs

Example configurations of expiratory limbs will now be described. The various embodiments described herein and illustrated in the figures are intended to be illustrative of various implementations that achieve a stated goal of reducing condensation in a ventilator and/or rain out in the expiratory limb. Many different variations and permutations are possible which do not depart from the scope of the examples provided herein. Thus, it is to be understood that the following examples should not be interpreted as limiting the scope of the disclosure, and the scope of the present disclosure extends beyond these enumerated examples.

Generally, the example expiratory limb designs can be configured to address situations where radiation of energy from the expiratory limb to ambient or the external atmosphere can cause too rapid a temperature drop at the entrance to the expiratory limb, which can cause condensation in this section of the limb. This situation can be common when the external temperature is relatively low, flow rate is relatively low and/or external relative humidity is relatively high (factors which can reduce breathability of the expiratory limb). Under such conditions it may be advantageous to decrease the rate of temperature change.

Relatedly, if conditions are present that limit or reduce the breathability of the expiratory limb, then it may be advantageous to have a relatively high exit temperature to limit condensation at the exit of the limb (e.g., upon entering the ventilator or gas source). For example, where the external relative humidity is relatively high or when the flow rate is relatively high, the breathability of the expiratory limb may be reduced.

Thus, example expiratory limbs are included and described herein that can be configured to deal with a wide range of conditions that may cause condensation. These designs could be modified where it is more desirable to address one condition over another or to enhance or improve efficacy related to a particular problem. The expiratory limbs presented herein can be configured to address situations where external temperature is relatively low, flow rate is relatively low, or external relative humidity is relatively high.

FIG. 3 illustrates an expiratory limb 210 with varying insulation 214 to control the temperature of the gas along the limb. The single conduit has several different sections having different insulation values. The insulation values are represented in FIG. 3 as different sizes of insulating material 214. However, the physical sizes of the insulating elements 214 do not have to decrease along the length and the sizes can be substantially identical along the length. To increase the effect of insulating elements 214, a thickness of the insulating material 214 can be increased, a density of the insulating material 214 can be increased, different materials can be used, etc. The insulating values can be configured to provide a relatively linear or slightly concave temperature profile over a range of temperature conditions, relative humidity, and/or flow rates. In some embodiments, the insulation sections along the limb are not discrete, but can be substantially continuous, or it can be configured to have insulation sections that change in a substantially continuous manner combined with sections that provide a discrete change in insulation value. The number of insulating sections can be any suitable number including, for example, 2, 3, 4, 5, 6, 7, 8, 10, 15, 20, 50, or more.

FIG. 4 illustrates an expiratory limb 210 with two sections that include breathable insulation 214 to control a temperature drop at a beginning of the limb and at an end of the limb. This configuration may be advantageous because the insulation material 214 is used where gas tends to experience relatively rapid cooling. The insulation values, extent of insulation, and placement of the insulation 214 can be configured to provide the advantages described herein. Additional insulating sections may be included as well.

FIG. 5 illustrates a expiratory limb 210 having multiple heater wires 212 that have a pitch spacing that is different in different sections or a single heater wire 212 with varying pitch spacing or a combination of both. This represents an active temperature control mechanism. As such, the heater wire or wires 212 can be coupled to the controller 122, as described herein with reference to FIG. 1, with the attendant control mechanisms described there. Similarly, the heater wires illustrated in FIGS. 4-9 can be controlled using the heater wire.

The heater wires 212 can be configured to be outside the tubing and can have different spacing along the limb. Near the patient end, the spacing can be relatively close together to generate or apply more heat compared to the heat applied closer to the limb exit. In some embodiments, there can be different zones with different winding densities to achieve a near linear temperature profile. In some embodiments, the number of sections with different spacing can be 2, 3, 4, 5, 6, 7, 8, 10, 15, 20, 25, 50, or more or the spacing of the windings can increase substantially smoothly with distance from the patient end. In some embodiments, the heater wire 212 comprises multiple, individual heating elements which can be collectively and/or individually controlled.

FIG. 6 illustrates an expiratory limb 210 having a coiled heater wire 212 that has a pitch spacing that is different in different sections. The heater wire 212 can be positioned within the limb. The winding configuration can be similar to the configurations described herein with reference to FIG. 5. In some embodiments, the heater wire 212 comprises multiple, individual heating elements which can be collectively and/or individually controlled.

FIG. 7 illustrates an expiratory limb 210 having a straight heater wire with zones of varying pitch spacing within the wire. The pitch spacing can be configured similar to the winding density and spacing described herein with reference to FIGS. 5 and 6. In some embodiments, the heater wire 212 comprises multiple, individual heating elements which can be collectively and/or individually controlled.

FIG. 8 illustrates an expiratory limb 210 having multiple heater sections wherein a system is configured to independently control the different sections of heater wire 212. As shown, the heater is divided into sections which can be selectively controlled by the controller 122 through the connectors 216a and 216b. There can be more sections with accompanying connectors, and the description here is limited to three sections with two connectors.

Connectors 216a and 216b couple the first and second heater segments and allow the controller to selectively apply heat to different sections of the expiratory limb 210. The connectors 216a, 216b can be configured to electrically couple the heater wires 212 in the segments to enable control of the heater wires 212 using the controller 122. The connector 216a, 216b can be configured to electrically couple temperature sensors (not shown) to enable the controller 122 to acquire their respective outputs. The connectors 216a, 216b can include electrical components that enable selective control of the heater wires 212. For example, the connectors 216a, 216b can include electrical components that direct power through the heater wires 212 in a first section in a first operation mode and through the heater wires 212 in both the first section and a second section in a second operation mode. The electrical components included on the connector 216a, 216b can include, for example and without limitation, resistors, diodes, transistors, relays, rectifiers, switches, capacitors, inductors, integrated circuits, micro-controllers, micro-processors, and the like. In some embodiments, the connector 216a, 216b can be configured to be internal to the expiratory limb 210 such that it is substantially shielded from external elements. In some embodiments, some of the electrical components on the connector 216a, 216b can be configured to be physically isolated from the humidified gas within the expiratory limb 210 to reduce or prevent damage that may result from exposure to humidity. In some embodiments, the connector 216a, 216b can include relatively inexpensive passive electrical components to reduce cost and/or increase reliability.

FIG. 9 illustrates an expiratory limb 210 having a heater wire 212 that is folded back upon itself at a patient end to control a temperature drop at a front end of the expiratory limb 210. The extent of the folding can be configured to provide a desired or advantageous temperature profile near the patient end of the limb 210. For example, it may be advantageous to limit the initial temperature drop to reduce condensation at the patient inlet so providing additional heat at this location may reduce or prevent rain out near the inlet.

FIG. 10 illustrates an expiratory limb 210 combining a varying insulation layer 214 with a heater wire 212 with a varying pitch. This embodiment is similar to combining the elements from FIG. 3 and FIG. 6. The sections of relatively constant insulation value and relatively constant winding density need not coincide. Transitions between insulation values and/or winding densities can be varied and can be independent from one another. This embodiment also illustrates that passive and active control approaches may be utilized in the expiratory limb 210.

Limbs with Non-Cylindrical Lumens and/or Multiple Lumens

FIGS. 11 through 33 illustrate some embodiments of limbs employing non-cylindrical or multi-lumen designs. As used herein, a multi-lumen limb is broadly defined to mean a limb having more than one lumen, such that the gas flow through one lumen is separated from the gas flow through any other lumen by at least one wall. Non-limiting embodiments of multi-lumen designs are shown in FIGS. 11A-19B, 26, 28, and 29-33. As used herein, a non-cylindrical limb is broadly defined to mean a limb having a lumen that is not shaped like a cylinder. Non-limiting embodiments of non-cylindrical designs are shown in FIGS. 20A-25B and 27. Certain embodiments can comprise a combination of such elements. For example, a limb can have a multi-lumen design comprising one or more non-cylindrical lumens.

In some embodiments, a multi-lumen limb comprises multiple conduits twisted or braided together. This may advantageously provide for reduced flow volume in the limb for the gas because the gas flow in each lumen is one third of the gas flow in a comparable single-lumen limb. The lower flow volume can increase the opportunity for evaporation from the wall surrounding the lumen. This configuration can also advantageously provide for an increased residence time in the limb for the gas because the length of the individual conduits is longer due at least in part to the twisting or braiding, while the overall length of the limb is a shorter standard commercial length. The increased residence time can increase the breathability of the limb at constant volumetric flow rate, as it increases the opportunity for evaporation from the wall surrounding the lumen.

Although the limb is described below with reference to an expiratory limb 210, it should be understood that such a limb is suitable for use in a variety of environments for transporting humidified air to or from a patient that would benefit from an increased residence time.

FIGS. 11A-19B illustrate various multi-lumen configurations. The multi-lumen limb 210 can include two or more individual conduits 211 joined together in various ways and in various geometrical configurations. In some embodiments, the conduits 211 are physically separated from one another to allow an increase in breathability through the conduit walls. In some embodiments, the limb 210 can include insulation material 214 surrounding the bundled conduits 211, as illustrated in FIGS. 16A-19B. Several geometrical configurations are illustrated in FIGS. 11A-19B, but other configurations are possible as well. For example, FIGS. 20A-25B, in particular, illustrate limbs 210 that do not comprise multiple individual conduits but which are configured to increase residence time using different cross-section shapes. FIGS. 24A-25B, in particular, illustrates that many different cross-section shapes are possible including regular or irregular shapes. In addition, any of the foregoing multi-lumen embodiments may include insulation material 214, as illustrated in FIGS. 24A-25B. In some embodiments, the shape of the conduit or conduits 211 can change along the length of the limb. For example, the conduit 211 can have a generally circular shape near the patient end which can change to a triangle at a point along the length, which can then change to a star shape or shape similar to any of the embodiments in FIGS. 20A-25B. This can change the surface area over the length of the limb, affecting the breathability and, hence, the temperature profile.

Figure 26:
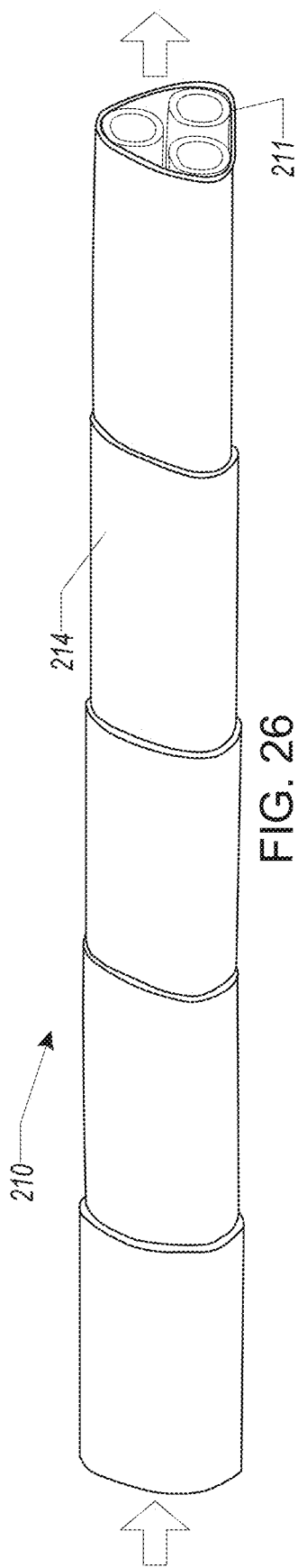
FIG. 26 illustrates a drying expiratory limb combining multiple lumens and varying insulation.

FIG. 26 illustrates a limb 210 combining multiple conduits 211 and varying insulation 214. This limb 210 represents a passive temperature control approach to the multi-lumen design. In some embodiments, using the multi-lumen design can increase the breathability of the limb 210. Using the insulation material 214 can decrease a rate of cooling that may increase where breathability increases. The insulation material can be configured to reduce cooling while not adversely affecting the breathability of the expiratory limb 210.

The individual conduits of a multi-lumen limb are desirably formed of a breathable material. In at least one embodiment, the individual conduits of a multi-lumen limb 210 are formed of corrugated foam as described in PCT Publication WO 2011/077250 and/or as commercially embodied in Evaqua 2™ conduits. Another suitable material is a breathable polyester thermoplastic elastomer having a porosity of about 14%. Such material is commercially embodied in Evaqua™ conduits. In at least one embodiment, each conduit of the multi-lumen limb is corrugated. The corrugated conduit can have a maximum outside diameter (at the corrugation peak) of 14.45 mm (or about 14.45 mm) or 15.15 mm (or about 15.15 mm). The corrugated conduit can have a minimum outside diameter (at the corrugation valley) of 12.7 mm (or about 12.7 mm). The period of the corrugation profile (the peak-to-peak distance) can be 3.14 mm (or about 3.14 mm). The amplitude of the corrugation (peak-to-valley distance) can be 1.7525 mm (or about 1.7525 mm). The wall thickness can be in the range of 0.5 mm and 1.0 mm (or in the range of about 0.5 mm and about 1.0 mm), and more particularly in the range of 0.6 mm and 0.9 mm (or in the range of about 0.6 mm and about 0.9 mm). For example, the wall thickness proximal corrugation peaks can be in the range of 0.50 mm and 0.65 mm (or in the range of about 0.5 mm and about 0.65 mm). As a further example, the wall thickness proximal corrugation valleys can be in the range of 0.80 mm and 1.0 mm (or about 0.80 mm and about 1.0 mm).

The conduit(s) can comprise reinforcing ribs, if desired. Such ribs are shown and described in conjunction with at least FIGS. 7A, 7B, 8A, and 8B of PCT Publication WO 2011/077250. Such ribs are also commercially embodied in Evaqua 2™ conduits. As described in the publication, these ribs are used to reinforce the foam and, among other things, lower the pneumatic compliance of the limb to acceptable values (less than 10 mL/kPa/m).

It was realized that the multi-lumen configuration can be self-reinforcing, which can reduce or eliminate a need for additional reinforcing structures such as internal or external ribs disposed on the conduit walls. Thus, the ribs can be eliminated in certain embodiments.

Eliminating the reinforcing ribs can be desirable because it can improve breathability. As shown in FIGS. 7A, 7B, 8A, and 8B of PCT Publication WO 2011/077250, the conduit wall thickness at the ribs is substantially greater than the conduit wall thickness between the ribs. The ribs therefore reduce the overall active (breathable) area of the limb. A multi-lumen construction without ribs according to this disclosure can have 15% (or about 15%) greater active area than an Evaqua 2™ conduit.

Table 2 compares the breathability of a multi-lumen limb comprising three individual conduits with various single-lumen limbs. All of the conduits/limbs are formed of the same foam material, as described in PCT Publication WO 2011/077250. The adult Evaqua 2™ limbs have reinforcing ribs, and the foam material has a void fraction of 0.35. The individual conduits of the multi-lumen limb do not have reinforcing ribs, and the foam material has a void fraction of 0.448. Limb A is an adult Evaqua 2™ limb with the gas stream heated with a heater cable. Limbs B and C are adult Evaqua 2™ limbs with the gas stream unheated. Limb D is the multi-lumen limb with the gas stream unheated. All experiments were conducted with a gas flow rate of 20 L/min through the sample limb, a nominal external temperature of 18-19° C. The runtime for the experiment was 6.5 hours with a total gas flow of 7,800 L. The inlet gas was estimated to be 36° C. at 98% relative humidity (RH). The results measured were the exit gas temperature, the dew point of the exit gas, the amount of water condensate outside the limb and the amount of water condensate in the limb at the end of the experiment.

TABLE 2

| BREATHABILITY PERFORMANCE | | | | |
| --- | --- | --- | --- | --- |
| | Limb A | Limb B | Limb C | Limb D |
| Flow, L/min | 20 | 20 | 20 | 20 |
| Outside Condensate, g | 2.2 | 5.8 | 6.7 | 0.9 |
| Inside Condensate, g | 0 | 22.0 | 22.8 | 0.0 |
| Total Condensate, g | 2.2 | 27.8 | 29.5 | 0.9 |
| Temperature exit gas, ° C. | 39.2 | 27.1 | 26.3 | 21.5 |
| Dew Point exit gas, ° C. | 32.71 | 26.73 | 25.85 | 21.45 |

The results show that Limb A has low total condensation, but a very high dew point. This increases the opportunity for condensation outside the limb, e.g., in the ventilator. Limbs B and C had much lower dew points for the exit gas than Limb A, but the total condensation was unacceptably high. The Limb D (the multi-lumen limb) had the lowest condensation of all samples, and the lowest dew point for the exit gas. Thus, Limb D had the lowest opportunity for condensation outside the limb in the ventilator.

The individual conduits of a multi-lumen limb 210 comprising a plurality of individual conduits without reinforcing ribs can have an unexpectedly high void fraction, while maintaining pneumatic compliance of less than 10 mL/kPa/m. In certain embodiments, the conduits of a multi-lumen limb comprising three individual conduits without reinforcing ribs have a void fraction in the range of 40% and 50% (or in the range of about 40% and about 50%), such as 45% (or about 45%), while the overall pneumatic compliance of the multi-lumen limb is less than 10 mL/kPa/m. This result is unexpected, as high-void fraction foam would be expected to be weak, and a foam conduit without ribs would be expected to be weaker still. Thus, one would ordinarily expect excessively high pneumatic compliance with such a configuration. As shown in Table 3, despite the higher void fraction and lack of reinforcing ribs in the component conduits, the multi-lumen limb has pneumatic compliance similar to that of the Evaqua 2™ limb, a corrugated, rib-reinforced, single-lumen foam limb, having a void fraction of 35%±4%.

Table 3 compares the pneumatic compliance of a multi-lumen sample and single-lumen limb samples. All of the conduits/limbs are formed of the same foam material, as described in PCT Publication WO 2011/077250. Limbs A-C are adult Evaqua 2™ limbs having reinforcing ribs, and the foam material has a void fraction of 0.35. Limb D is a three-lumen limb comprising three infant-size conduits without reinforcing ribs, and the foam material has a void fraction of 0.448.

TABLE 3

PNEUMATIC COMPLIANCE

| Limb | Average compliance, mL/kPa/m |
|---|---|
| A | 2.74 |
| B | 2.51 |
| C | 2.69 |
| D | 2.61 |

As shown in Table 3, although the individual conduits of Limb D do not have reinforcing ribs, Limb D has a pneumatic compliance comparable to that of Limbs A-C.

Figure 27:
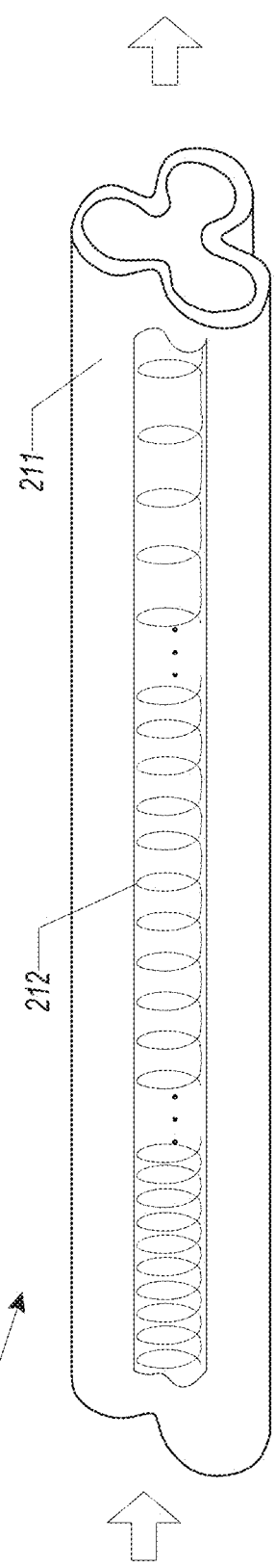
FIG. 27 illustrates a drying expiratory limb with a cross-section similar to the drying expiratory limbs illustrated in FIGS. 21A-21B and a heater wire with a varying pitch spacing along its length.
Figure 28:
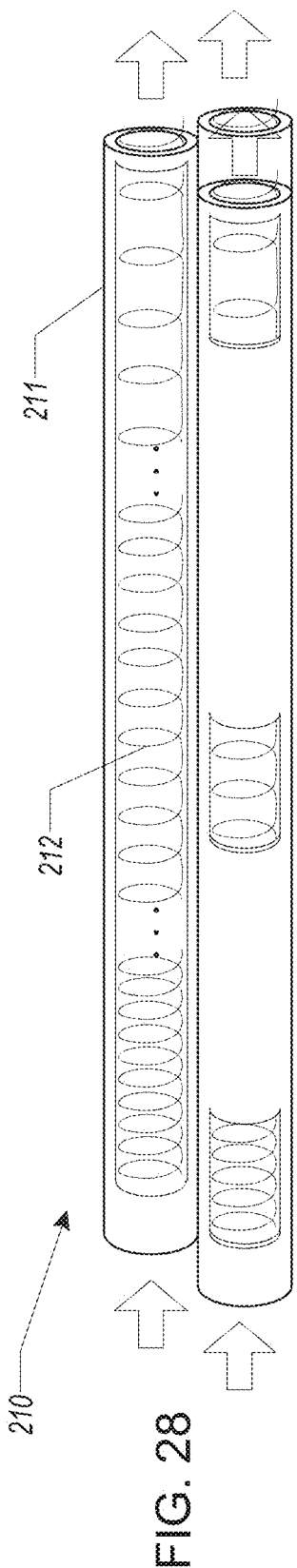
FIG. 28 illustrates a drying expiratory limb with a multi-lumen design in conjunction with heater wires in each lumen.
Figure 29:
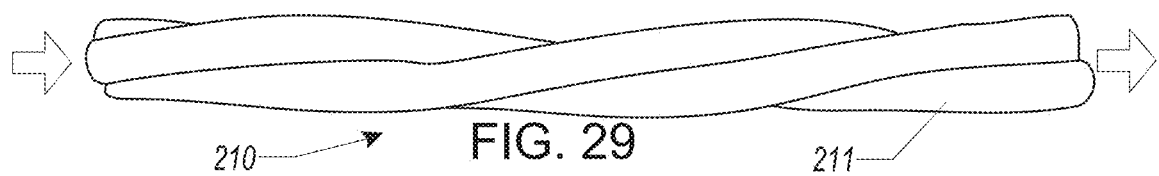
FIGS. 29-33 illustrate various multi-lumen configurations for a limb for conveying humidified gas in a medical circuit.

The limbs 210 illustrated in FIGS. 27 and 28 illustrate active approaches to temperature control in conjunction with the multi-lumen designs of FIGS. 11A-25B. FIG. 27 illustrates a limb 210 with a cross-section similar to the limbs 210 illustrated in FIGS. 24A-25B and a heater wire 212 with varying pitch spacing along its length, similar to the limbs described with reference to FIGS. 6 and 10.

Heater wires 212 can be used to limit the cooling of the gas that may arise due to excessively low external temperature. FIG. 28 illustrates a limb 210 with a multi-lumen design in conjunction with heater wires 212 in each individual conduit 211. The heater wire 212 can extend generally longitudinally along a length of individual conduit 211. For example, as shown in FIG. 28, the heater wire 212 can be spirally wound along substantially the full extent of each individual conduit 211. Nevertheless, the heater wire can extend along a shorter section. The heater wire 212 can be embedded or encapsulated in the wall of the individual conduit 211 or disposed inside the lumen. The heater wire 212 in FIG. 28 has a variable pitch. Alternatively, in spiral-wound configurations, the heater wire can have a regular pitch. Other suitable heater wire configurations are known in the art and are contemplated within the scope of this disclosure.

FIGS. 29-33 illustrate various multi-lumen configurations for a limb 210. As discussed above, the individual conduits 211 can be twisted around each other for mechanical stability and/or support. By twisting the individual conduits, each conduit's length is greater than the length of the resulting limb 210. This can increase the residence time the gas spends in the limb at constant volumetric flow rate, which can result in a more advantageous temperature profile, breathability, and reduction in rain out. In some embodiments, the multiple individual conduits 211 can be held together using adhesives. In some embodiments, the multiple individual conduits can be held together using securing mechanisms 215 such as clips, rubber bands, ties, or the like. In some embodiments, the individual conduits can be held together using a sheath 214, where the sheath 214 can also be insulating and/or the sheath 214 can be configure to be aesthetically pleasing. The number of twisted conduits can be, for example, 2, 3, 4, 5, or more than 5. In at least one embodiment, the limb 210 comprises three conduits.

Figure 34:
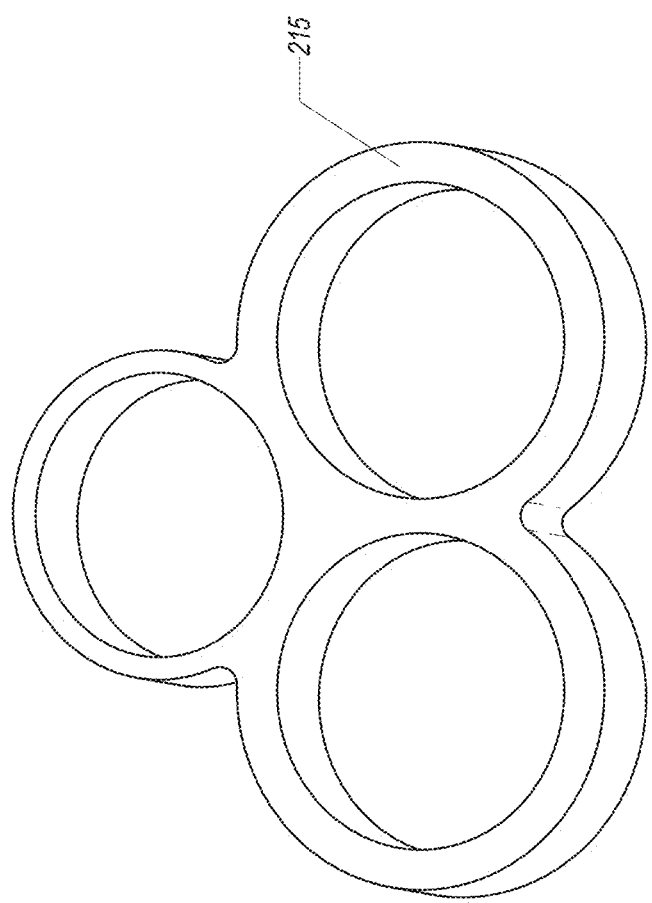
FIG. 34 illustrates a securing mechanism for use with a multi-lumen limb.

FIG. 34 shows an example securing mechanism 215 suitable for use with a three-conduit configuration for a limb. In this example, the securing mechanism 215 comprises a plurality of rings arranged in a trefoil. The securing mechanism 215 trefoil shown in FIG. 34 can be formed from an extruded plastic, metal, or foam material.

Figure 30:
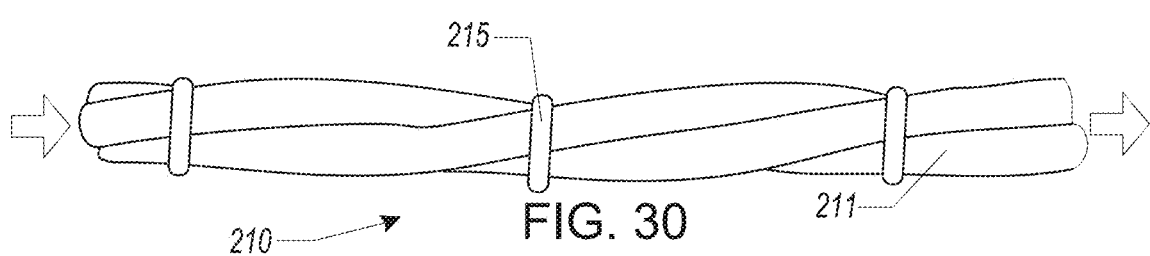
Figure 31:
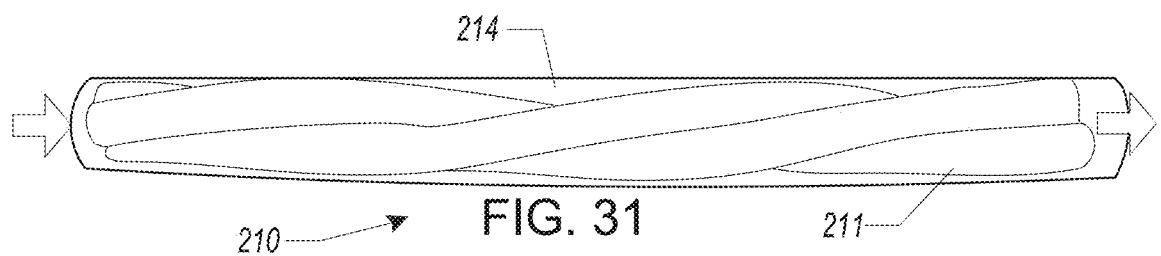
Figure 32:
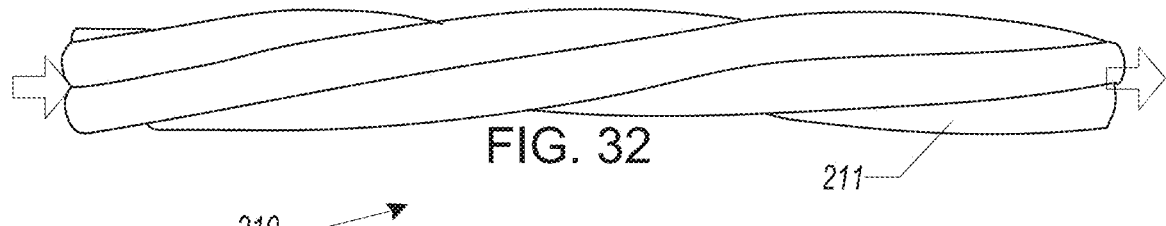
Figure 33:
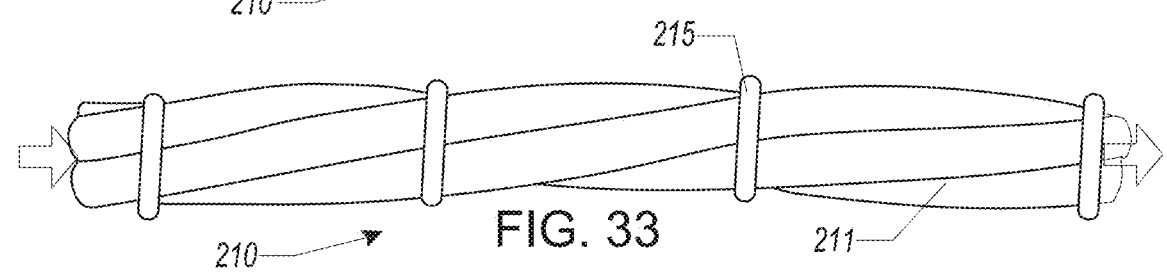

To assemble a limb as shown in FIG. 30, each of the three conduits 211 can be passed through one of the rings of a first securing mechanism 215 trefoil, shown in FIG. 34, and then twisted or braided. The three conduits 211 can then be passed through the rings of a second securing mechanism 215 trefoil placed at a desired distance from the first securing mechanism 215 trefoil, and then twisted or braided again. The three conduits 211 can then be passed through the rings of a third securing mechanism 215 trefoil placed at a desired distance from the second securing mechanism 215 trefoil, and twisted or braided yet again. The three conduits 211 need not be twisted or braided after passing through a securing mechanism 215 trefoil, however, if a looser configuration is desired. For example, the twisting or braiding can be eliminated after the three conduits 211 are passed through the rings of the second securing mechanism 215 trefoil. The twisting or braiding can also be eliminated entirely. In addition, when a tighter configuration is desired, the three conduits 211 can be twisted or braided multiple times between securing mechanisms 215. The method described herein does not imply a fixed order to the steps. Nor does it imply that any one step is required to practice the method. Embodiments may be practiced in any order and combination that is practicable.

Suitable spacing for the securing mechanism 215 trefoil can be in the range of 150 mm and 500 mm (or in the range of about 150 mm and about 500 mm), such as 250 mm or thereabout. In some embodiments, a plurality of securing mechanisms 215, for example, a number in the range of 2 and 9, such as 2 or 3, can be placed along a commercially-standard length of tubing. Desirably, the securing mechanisms 215 are evenly or about evenly spaced from each other and from both ends. For example, when two securing mechanisms 215 are used, the one securing mechanisms can be placed at the ⅓ length position and one securing mechanism can be placed at the ⅔ length position. Two securing mechanism 215 can be spaced 500 mm (or about 500 mm) apart. Nine securing mechanisms 215 can be spaced 150 (or about 150 mm) apart. Fewer securing mechanisms can be employed in a twisted or braided configuration.

The foregoing spacing configurations have been found to prevent the individual conduits from separating, while not significantly reducing breathability. It was also discovered that, when the securing mechanism 215 trefoils are placed sufficiently close together (e.g., at a spacing of about 250 mm), the corrugation on the outside of the conduit 211 creates enough friction that the twists does not easily untwist. It was further discovered that the number of securing mechanisms 215 holding the individual conduits 211 together does not significantly impact the overall compliance of the limb. Table 4 shows the results of compliance testing for a three-conduit 211 limb configuration with different number of securing mechanism 215 trefoils. By way of comparison, Table 5 provides results of compliance testing for single conduit limbs. All of the conduits/limbs described in Tables 4 and 5 formed of the same foam material, as described in PCT Publication WO 2011/077250. The limb in Table 4 is a three-lumen limb comprising three infant-size conduits without reinforcing ribs, and the foam material has a void fraction of 0.448. The "adult" limb in Table 5 is a 24-mm-outer-diameter Evaqua 2™ limb having reinforcing ribs, and the foam material has a void fraction of 0.35. The "infant" limb in Table 5 is a 15-mm-outer-diameter Evaqua 2™ limb without reinforcing ribs, and the foam material has a void fraction of 0.448.

TABLE 4

PNEUMATIC COMPLIANCE AS A FUNCTION OF NUMBER OF SECURING MECHANISMS

| No. of Securing Mechanisms | Volume Infused, mL | Pressure, kPa | Volume/ Pressure Ratio | Average compliance, mL/kPa/m |
| --- | --- | --- | --- | --- |
| 1 | 36.69 | 5.997 | 6.12 | 4.08 |
| 2 | 37.589 | 6.148 | 6.11 | 4.08 |
| 3 | 35.887 | 6.006 | 5.98 | 3.98 |
| 4 | 36.105 | 6.046 | 5.97 | 3.98 |
| 5 | 36.427 | 6.044 | 6.03 | 4.02 |

TABLE 5

PNEUMATIC COMPLIANCE OF SINGLE CONDUIT LIMBS

| Limb | Volume Infused, mL | Pressure, kPa | Average compliance, mL/kPa/m |
| --- | --- | --- | --- |
| Adult | 32.022 | 6.027 | 3.54 |
| Infant | 12.180 | 6.048 | 1.34 |

The above-described trefoil shape is provided as an example. A different number of conduits 211 will necessitate a different number of rings. For example, a securing mechanism 215 comprising four rings arranged in a quatrefoil can be used with a four-conduit configuration; a securing mechanism 215 comprising five rings arranged in a cinquefoil can be used with a five-conduit configuration; and so forth. In addition, while the foregoing examples describe generally symmetrical multi-lobed shapes, asymmetrical configurations of the rings are also contemplated.

FIGS. 35A-35E show a three-way connector 301 suitable for use on one or both ends of a three-lumen limb 210. The connector 301 is preferably a molded component formed from a suitable material such as plastic, such as polypropylene or polytetrafluoroethylene.

The three-way connector 301 comprises a unitary portion 305 and a tripartite portion 307. The unitary portion 305 comprises a conduit suitable for connecting to port of a device, such as a humidifier or a pressurized gas source, or to a port of a patient interface, such as a nasal cannula, a face mask, a nasal mask, a nasal/pillow mask. Desirably, the conduit of the unitary portion 305 has a standard-size medical taper suitable for use with the desired device or patient interface. As shown in greater detail in FIG. 35E, the tripartite portion 307 comprises three conduits 311 each suitable for connecting to a conduit 211.

Figure 35B:
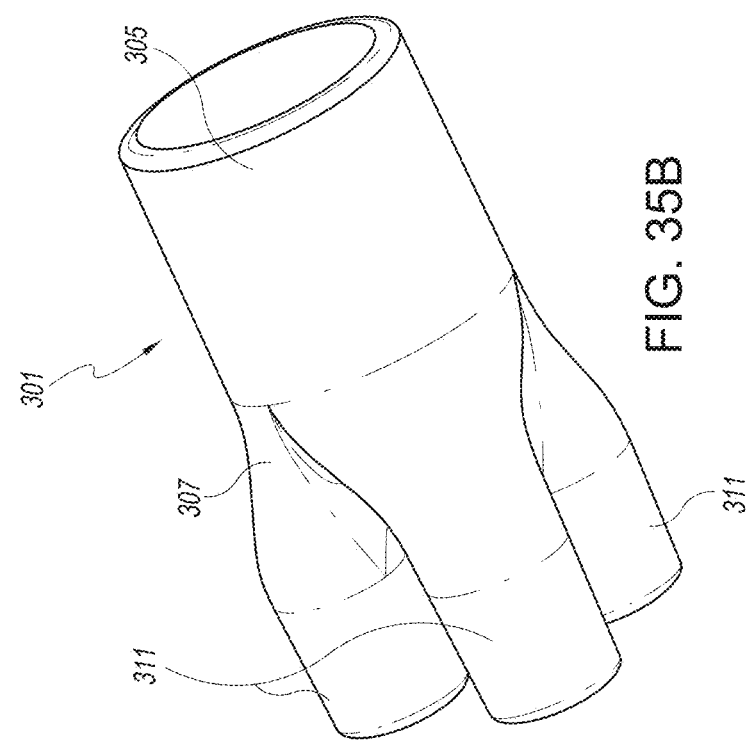
FIGS. 35A-35D illustrate a connector for use with one or both ends of a multi-lumen limb.
Figure 35A:
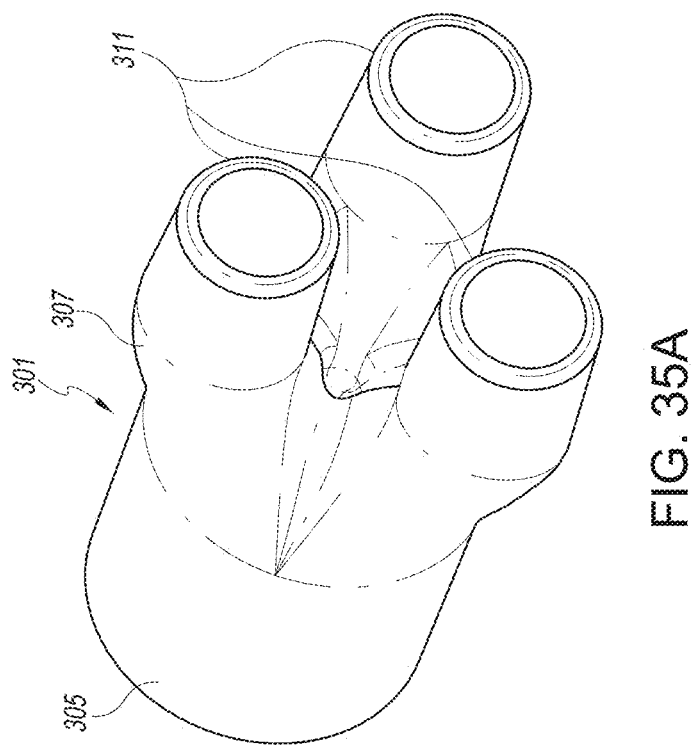
Figure 35D:
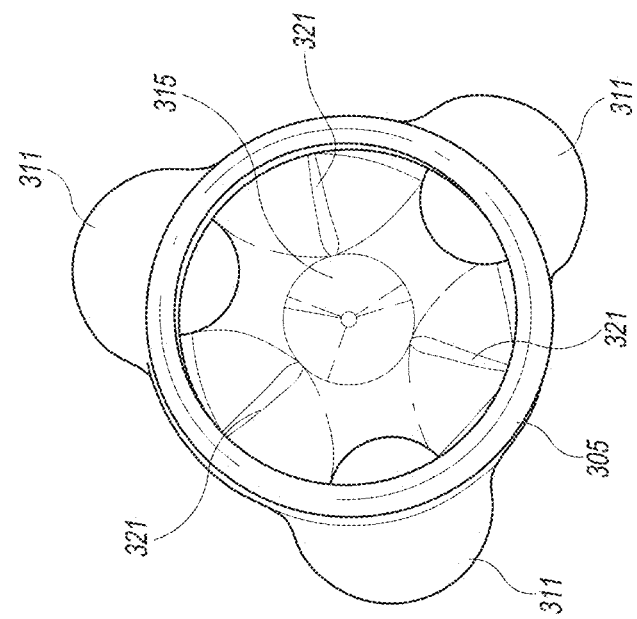
Figure 35C:
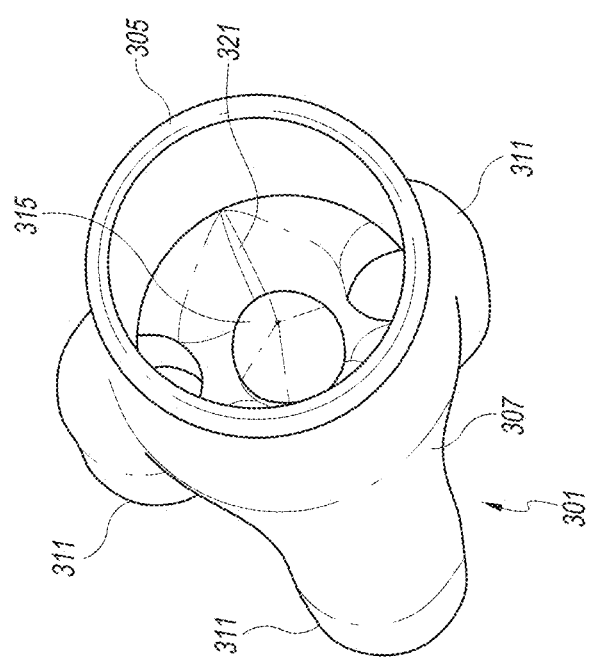
Figure 35E:
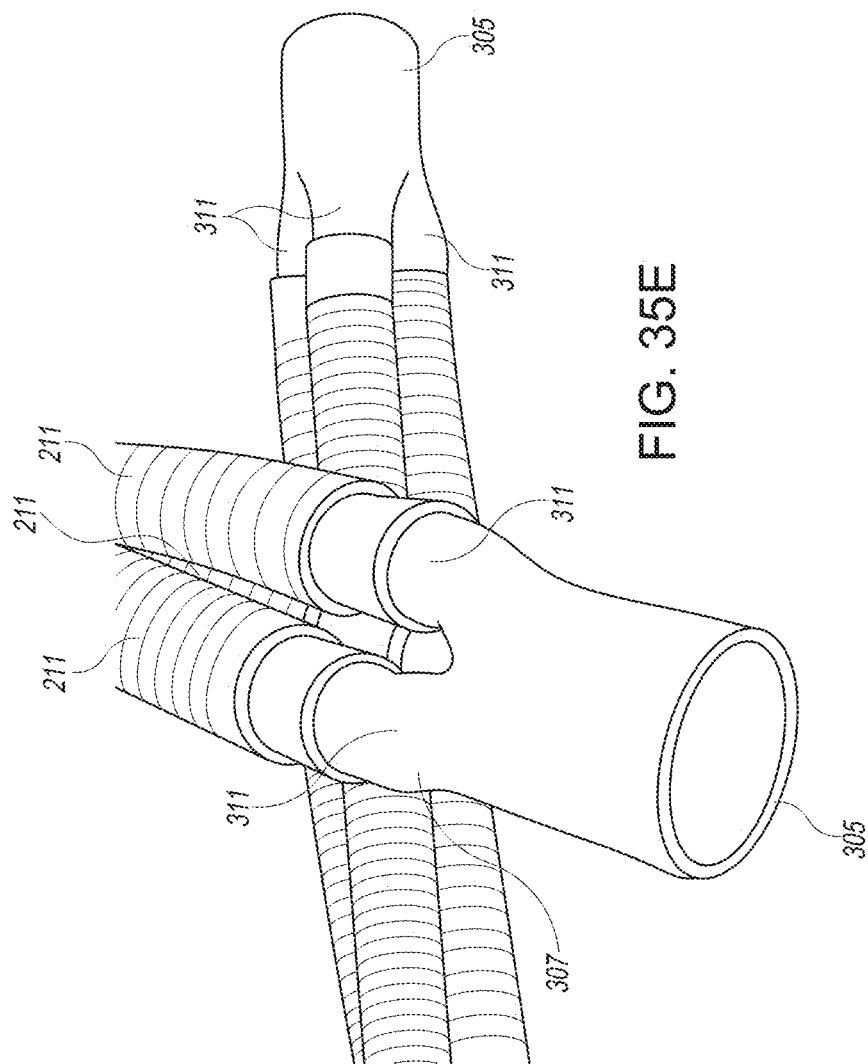
FIG. 35E illustrates the connector in use on a multi-lumen limb.

As shown in FIGS. 35C and 35D, the three-way connector 301 can comprise an internal ogive 315. As used herein, ogive is defined to mean a tapered, streamlined, three-dimensional object generally resembling a bullet or torpedo. In FIGS. 35C and 35D, the leading edge of the ogive 315 is pointed. Nevertheless, the term is used herein in its broadest sense and encompasses shapes having a pointed, rounded, or blunt leading edge, and includes without limitation cones, pyramids or tetrahedrons, truncated cones, truncated pyramids or tetrahedrons, and other truncated ogives. The base (widest portion) of the ogive 315 is situated proximal the tripartite portion 307. The ogive 315 tapers in the direction of the unitary portion 305. The ogive 315 can more evenly divide the gas flow from the unitary portion 301 into the three conduits 311 of the tripartite portion 307. The ogive 315 can also more evenly combine gas flow from the three conduits 311 of the tripartite portion 307 as the gas flow enters the unitary portion 301 and promote laminar flow.

CONCLUSION

Examples of various limbs for use with medical circuits have been described with reference to the figures. The representations in the figures have been presented to clearly illustrate principles described herein, and details regarding divisions of modules or systems have been provided for ease of description rather than attempting to delineate separate physical embodiments. The examples and figures are intended to illustrate and not to limit the scope of the embodiments described herein. For example, the principles herein may be applied to limbs for use in other circuits as well as respiratory circuits, including surgical humidifiers.

As used herein, the term "processor" refers broadly to any suitable device, logical block, module, circuit, or combination of elements for executing instructions. For example, the controller 122 can include any conventional general purpose single- or multi-chip microprocessor such as a Pentium® processor, a MIPS® processor, a Power PC® processor, AMD® processor, ARM® processor, or an ALPHA® processor. In addition, the controller 122 can include any conventional special purpose microprocessor such as a digital signal processor. The various illustrative logical blocks, modules, and circuits described in connection with the embodiments disclosed herein can be implemented or performed with a general purpose processor, a digital signal processor (DSP), an application specific integrated circuit (ASIC), a field programmable gate array (FPGA), or other programmable logic device, discrete gate or transistor logic, discrete hardware components, or any combination thereof designed to perform the functions described herein. Controller 122 can be implemented as a combination of computing devices, e.g., a combination of a DSP and a microprocessor, a plurality of microprocessors, one or more microprocessors in conjunction with a DSP core, or any other such configuration.

Data storage can refer to electronic circuitry that allows information, typically computer or digital data, to be stored and retrieved. Data storage can refer to external devices or systems, for example, disk drives or solid state drives. Data storage can also refer to fast semiconductor storage (chips), for example, Random Access Memory (RAM) or various forms of Read Only Memory (ROM), which are directly connected to the communication bus or the controller 122. Other types of memory include bubble memory and core memory. Data storage can be physical hardware configured to store information in a non-transitory medium.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments. As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y and Z," unless specifically stated otherwise, is otherwise understood with the context as used in general to convey that an item, term, etc. may be either X, Y or Z. Thus, such conjunctive language is not generally intended to imply that certain embodiments require at least one of X, at least one of Y and at least one of Z each to be present.

It should be emphasized that many variations and modifications may be made to the embodiments described herein, the elements of which are to be understood as being among other acceptable examples. All such modifications and variations are intended to be included herein within the scope of this disclosure and protected by the following claims. Further, nothing in the foregoing disclosure is intended to imply that any particular component, characteristic or process step is necessary or essential.

What is claimed is:

1. A multi-lumen breathable expiratory limb suitable for use in a medical circuit, the expiratory limb comprising a plurality of discrete conduits, each of the plurality of discrete conduits comprising a wall, the wall extending from an inlet end to an outlet end, the inlet end being configured to receive gas from a patient interface, the wall being formed of a foam material that comprises a void fraction of between 40% and 50%, and an overall pneumatic compliance of the expiratory limb being less than 10 mL/kPA/m.

2. The expiratory limb of claim 1, wherein the inlet end is connected to an inlet port and the outlet end is connected to an outlet port.

3. The expiratory limb of claim 1, wherein the plurality of discrete conduits comprises less than six discrete conduits.

4. The expiratory limb of claim 3, wherein the plurality of discrete conduits consists of three discrete conduits.

5. The expiratory limb of claim 1, wherein each of the plurality of discrete conduits comprises a corrugated wall.

6. The expiratory limb of claim 5, wherein one or more of the plurality of discrete conduits comprises a maximum outside diameter of about 14.45 mm or about 15.15 mm.

7. The expiratory limb of claim 5, wherein one or more of the plurality of discrete conduits comprises a minimum outside diameter of about 12.7 mm.

8. The expiratory limb of claim 5, wherein one or more of the plurality of discrete conduits comprises a corrugation period of about 3.14 mm.

9. The expiratory limb of claim 5, wherein one or more of the plurality of discrete conduits comprises a corrugation amplitude of about 1.7525 mm.

10. The expiratory limb of claim 5, wherein one or more of the plurality of discrete conduits comprises a wall thickness that is within a range of about 0.5 mm to about 1.0 mm.

11. The expiratory limb of claim 10, wherein the wall thickness is within a range of about 0.6 mm to about 0.9 mm.

12. The expiratory limb of claim 10, wherein the wall thickness proximal a peak of the corrugated wall is within a range of about 0.5 mm and 0.65 mm.

13. The expiratory limb of claim 10, wherein the wall thickness proximal a valley of the corrugated wall is within a range of about 0.8 mm and 1.0 mm.

14. The expiratory limb of claim 1, wherein the wall of each of the plurality of discrete conduits do not comprise longitudinal reinforcing ribs.

15. The expiratory limb of claim 1, wherein the foam material comprises a void fraction of about 45%.

16. The expiratory limb of claim 1, wherein the plurality of discrete conduits are twisted or braided together.

17. The expiratory limb of claim 16, wherein the plurality of discrete conduits are connected together through at least one securing mechanism, the at least one securing mechanism comprising a plurality of openings that correspond to the plurality of discrete conduits.

18. The expiratory limb of claim 1, wherein the plurality of discrete conduits are formed of a breathable polyester thermoplastic elastomer.

19. The expiratory limb of claim 1, wherein the wall of each of the plurality of discrete conduits comprise a breathable material.

* * * * *